US012576215B2

(12) United States Patent
Kemp et al.

(10) Patent No.: US 12,576,215 B2
(45) Date of Patent: *Mar. 17, 2026

(54) AUTOINJECTOR AND METHOD OF ASSEMBLING

(71) Applicant: SANOFI-AVENTIS DEUTSCHLAND GMBH, Frankfurt am Main (DE)

(72) Inventors: Thomas Mark Kemp, Ashwell (GB); Carsten Mosebach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 921 days.

This patent is subject to a terminal disclaimer.

(21) Appl. No.: 17/391,193

(22) Filed: Aug. 2, 2021

(65) Prior Publication Data

US 2022/0016358 A1 Jan. 20, 2022

Related U.S. Application Data

(63) Continuation of application No. 15/579,024, filed as application No. PCT/EP2016/062462 on Jun. 2, 2016, now Pat. No. 11,103,649.

(30) Foreign Application Priority Data

Jun. 3, 2015 (EP) .................................... 15170597

(51) Int. Cl.
*A61M 5/32* (2006.01)
*A61M 5/20* (2006.01)
(Continued)

(52) U.S. Cl.
CPC ........ *A61M 5/3204* (2013.01); *A61M 5/2033* (2013.01); *A61M 2005/2013* (2013.01);
(Continued)

(58) Field of Classification Search
CPC .... A61M 2005/2013; A61M 2205/581; A61M 2207/00; A61M 5/2033; A61M 5/3157; A61M 5/3204

See application file for complete search history.

(56) References Cited

U.S. PATENT DOCUMENTS

| | | | |
|---|---|---|---|
| 3,026,873 | A | 3/1962 | Miskel et al. |
| 3,076,455 | A | 2/1963 | McConnaughey et al. |

(Continued)

FOREIGN PATENT DOCUMENTS

| | | |
|---|---|---|
| CA | 2212489 | 2/1998 |
| CN | 101022841 | 5/2005 |

(Continued)

OTHER PUBLICATIONS

*SHL Medical AG* (Inventors: Anders Holmqvist, and Hsueh-Yi Chen) Junior Party (U.S. Appl. No. 17/020,027), v. *Sanofi-Aventis Deutschland GMBH* (Inventors: Yannick Hourmand, Douglas Ivan Jennings, and Matthew Ekman), Senior Party (U.S. Appl. No. 17/020,027), Patent Interference No. 106,135, Decision on Motions, dated Jul. 29, 2022, 40 pages.

(Continued)

*Primary Examiner* — Bhisma Mehta
*Assistant Examiner* — Adam J. Cermak
(74) *Attorney, Agent, or Firm* — Fish & Richardson P.C.

(57) ABSTRACT

The disclosure further relates to an autoinjector and a method of assembling the autoinjector. A syringe carrier is disclosed comprising a housing adapted to receive a syringe. They syringe includes a needle encapsulated by a removable protective needle sheath. The syringe carrier further includes two or more flexible arms protruding outwards in a relaxed state and adapted to couple with the syringe in a mounted (Continued)

position. In the mounted position, the flexible arms deflect radially inwards due, in part, to an axial force operating on the syringe carrier.

22 Claims, 15 Drawing Sheets

(51) Int. Cl.
  *A61M 5/24*          (2006.01)
  *A61M 5/315*         (2006.01)
(52) U.S. Cl.
  CPC .............. *A61M 2005/2407* (2013.01); *A61M 2005/2437* (2013.01); *A61M 2005/244* (2013.01); *A61M 5/3157* (2013.01); *A61M 2205/581* (2013.01); *A61M 2207/00* (2013.01)

(56)                References Cited

U.S. PATENT DOCUMENTS

| | | | |
|---|---|---|---|
| 3,144,178 A * | 8/1964 | Sarnoff | A61M 5/24 |
| | | | 222/327 |
| 3,783,997 A * | 1/1974 | Brown | A61M 5/24 |
| | | | 604/193 |
| 3,880,163 A | 4/1975 | Ritterskamp | |
| 4,563,175 A | 1/1986 | Lafond | |
| 4,643,724 A | 2/1987 | Jobe | |
| 4,655,751 A | 4/1987 | Harbaugh | |
| 4,735,311 A | 4/1988 | Lowe et al. | |
| 4,838,857 A | 6/1989 | Strowe et al. | |
| 4,871,355 A | 10/1989 | Kikkawa | |
| 4,909,791 A | 3/1990 | Norelli | |
| 4,931,040 A | 6/1990 | Haber et al. | |
| 4,946,447 A | 8/1990 | Hardcastle et al. | |
| 4,964,866 A | 10/1990 | Szwarc | |
| 4,973,318 A | 11/1990 | Holm et al. | |
| 4,990,142 A | 2/1991 | Hoffman et al. | |
| 4,997,422 A | 3/1991 | Chow et al. | |
| 5,000,744 A | 3/1991 | Hoffman et al. | |
| 5,078,698 A * | 1/1992 | Stiehl | A61M 5/24 |
| | | | 604/235 |
| 5,085,641 A | 2/1992 | Sarnoff et al. | |
| 5,137,516 A * | 8/1992 | Rand | A61M 5/28 |
| | | | 604/137 |
| 5,163,918 A | 11/1992 | Righi et al. | |
| 5,169,392 A | 12/1992 | Ranford et al. | |
| 5,282,793 A | 2/1994 | Larson | |
| 5,290,255 A | 3/1994 | Vallelunga et al. | |
| 5,320,609 A | 6/1994 | Haber et al. | |
| 5,322,511 A | 6/1994 | Armbruster et al. | |
| 5,344,407 A | 9/1994 | Ryan | |
| 5,350,367 A | 9/1994 | Stiehl et al. | |
| 5,356,395 A * | 10/1994 | Chen | A61M 5/3213 |
| | | | 604/263 |
| 5,368,578 A | 11/1994 | Covington et al. | |
| 5,383,858 A | 1/1995 | Reilly et al. | |
| 5,383,863 A | 1/1995 | Mardones | |
| 5,439,450 A | 8/1995 | Haedt | |
| 5,451,214 A | 9/1995 | Hajishoreh | |
| 5,480,387 A | 1/1996 | Gabriel et al. | |
| 5,520,653 A | 5/1996 | Reilly et al. | |
| 5,599,309 A | 2/1997 | Marshall et al. | |
| 5,637,101 A | 6/1997 | Shillington | |
| 5,709,662 A | 1/1998 | Olive et al. | |
| 5,779,675 A | 7/1998 | Uber et al. | |
| 5,855,839 A * | 1/1999 | Brunel | A61M 5/24 |
| | | | 604/110 |
| 5,865,805 A | 2/1999 | Ziemba | |
| 5,913,844 A | 6/1999 | Fago et al. | |
| 5,925,032 A | 7/1999 | Clements | |
| 5,928,205 A * | 7/1999 | Marshall | A61M 5/24 |
| | | | 604/232 |
| 5,928,698 A | 7/1999 | Soyad | |
| 6,059,756 A | 5/2000 | Yeh | |
| 6,090,082 A | 7/2000 | King et al. | |
| 6,203,530 B1 | 3/2001 | Stewart | |
| 6,210,369 B1 | 4/2001 | Wilmot et al. | |
| 6,258,068 B1 * | 7/2001 | Kirchhofer | A61M 5/315 |
| | | | 128/DIG. 1 |
| 6,371,939 B2 | 4/2002 | Bergens et al. | |
| 6,454,743 B1 | 9/2002 | Weber | |
| 6,544,234 B1 | 4/2003 | Gabriel | |
| 6,613,022 B1 | 9/2003 | Doyle | |
| 6,656,163 B1 | 12/2003 | Marshall et al. | |
| 6,726,657 B1 | 4/2004 | Dedig et al. | |
| 6,743,205 B2 | 6/2004 | Nolan, Jr. et al. | |
| 7,118,552 B2 | 10/2006 | Shaw et al. | |
| 7,288,078 B2 | 10/2007 | Fitzgerald | |
| 7,717,877 B2 | 5/2010 | Lavi et al. | |
| 7,955,303 B2 | 6/2011 | Burren et al. | |
| 8,647,299 B2 | 2/2014 | Stamp | |
| 8,845,594 B2 | 9/2014 | Jennings | |
| 8,876,785 B2 | 11/2014 | Holmqvist | |
| 8,900,197 B2 * | 12/2014 | Crow | A61M 5/2033 |
| | | | 604/197 |
| 8,992,746 B2 | 3/2015 | Miyaji et al. | |
| 9,072,833 B2 | 7/2015 | Jennings et al. | |
| 9,199,041 B2 * | 12/2015 | Edginton | A61M 5/2033 |
| 9,216,256 B2 | 12/2015 | Olson et al. | |
| 9,233,213 B2 | 1/2016 | Olson et al. | |
| 9,242,053 B2 | 1/2016 | Wozencroft | |
| 9,289,554 B2 | 3/2016 | Hourmand et al. | |
| 9,408,970 B2 * | 8/2016 | Hourmand | A61M 5/24 |
| 9,408,976 B2 | 8/2016 | Olson et al. | |
| 9,713,678 B2 | 7/2017 | Hourmand et al. | |
| 9,757,520 B2 | 9/2017 | Corrigan | |
| 9,867,940 B2 | 1/2018 | Holmqvist et al. | |
| 10,420,898 B2 | 9/2019 | Daniel | |
| 10,434,258 B2 | 10/2019 | Hourmand et al. | |
| 10,441,719 B2 | 10/2019 | Hourman et al. | |
| 10,646,656 B2 | 5/2020 | Hourmand et al. | |
| 10,881,799 B2 | 1/2021 | Hirschel et al. | |
| 10,918,803 B2 | 2/2021 | Kemp et al. | |
| 11,097,065 B2 * | 8/2021 | Newton | A61M 5/3204 |
| 11,103,649 B2 * | 8/2021 | Kemp | A61M 5/3204 |
| 11,400,221 B2 | 8/2022 | Hourmand et al. | |
| 11,400,222 B2 | 8/2022 | Hourmand et al. | |
| 11,400,223 B2 | 8/2022 | Hourmand et al. | |
| 11,406,763 B2 | 8/2022 | Hourmand et al. | |
| 11,406,764 B2 | 8/2022 | Hourmand et al. | |
| 11,511,043 B2 | 11/2022 | Hourmand et al. | |
| 11,980,744 B2 | 5/2024 | Hourmand et al. | |
| 12,102,799 B2 | 10/2024 | Hourmand et al. | |
| 12,102,800 B2 | 10/2024 | Hourmand et al. | |
| 12,102,801 B2 | 10/2024 | Hourmand et al. | |
| 12,102,802 B2 | 10/2024 | Hourmand et al. | |
| 12,102,803 B2 | 10/2024 | Hourmand et al. | |
| 12,318,597 B2 | 6/2025 | Kemp et al. | |
| 2001/0011163 A1 | 8/2001 | Nolan, Jr. et al. | |
| 2002/0083564 A1 | 7/2002 | James | |
| 2003/0105430 A1 | 6/2003 | Lavi et al. | |
| 2003/0163092 A1 * | 8/2003 | Parker | A61M 5/326 |
| | | | 604/198 |
| 2004/0010234 A1 * | 1/2004 | Hung | A61M 5/3243 |
| | | | 604/198 |
| 2004/0039336 A1 | 2/2004 | Amark et al. | |
| 2004/0108339 A1 | 6/2004 | Hansen et al. | |
| 2004/0267199 A1 | 12/2004 | Marshall et al. | |
| 2005/0020979 A1 | 1/2005 | Westbye et al. | |
| 2005/0027255 A1 | 2/2005 | Lavi et al. | |
| 2005/0075608 A1 | 4/2005 | Holdgate et al. | |
| 2005/0101919 A1 | 5/2005 | Brunnberg | |
| 2005/0115507 A1 | 6/2005 | Halachmi et al. | |
| 2005/0165353 A1 | 7/2005 | Pessin | |
| 2005/0277896 A1 | 12/2005 | Messerli et al. | |
| 2006/0036216 A1 | 2/2006 | Rimlinger et al. | |
| 2006/0100588 A1 * | 5/2006 | Brunnberg | A61M 5/3213 |
| | | | 128/919 |
| 2006/0161114 A1 | 7/2006 | Perot et al. | |
| 2006/0167412 A1 | 7/2006 | Marshall | |
| 2006/0184133 A1 | 8/2006 | Pessin | |
| 2007/0173770 A1 | 7/2007 | Stamp | |
| 2007/0260348 A1 | 11/2007 | Gordils | |

(56) References Cited

U.S. PATENT DOCUMENTS

| | | | |
|---|---|---|---|
| 2008/0147003 A1 | 6/2008 | Menzi et al. | |
| 2008/0228143 A1 | 9/2008 | Stamp | |
| 2008/0262427 A1 | 10/2008 | Hommann | |
| 2009/0012471 A1 | 1/2009 | Harrison | |
| 2009/0105663 A1 | 4/2009 | Brand et al. | |
| 2009/0254027 A1 | 10/2009 | Moeller | |
| 2010/0152655 A1 | 6/2010 | Stamp | |
| 2010/0179507 A1 | 7/2010 | Hess et al. | |
| 2010/0185178 A1 | 7/2010 | Sharp et al. | |
| 2011/0282278 A1 * | 11/2011 | Stamp | A61M 5/2033 604/110 |
| 2012/0053528 A1 | 3/2012 | Bollenbach et al. | |
| 2012/0130321 A1 | 5/2012 | Woehr | |
| 2012/0186075 A1 * | 7/2012 | Edginton | A61M 5/24 29/700 |
| 2012/0203186 A1 | 8/2012 | Vogt et al. | |
| 2013/0131602 A1 * | 5/2013 | Kemp | A61M 5/3202 604/197 |
| 2013/0204195 A1 * | 8/2013 | Ekman | A61M 5/2033 604/220 |
| 2013/0220869 A1 | 8/2013 | Klintenstedt et al. | |
| 2013/0274678 A1 * | 10/2013 | Roberts | A61M 5/3243 604/198 |
| 2014/0243753 A1 | 8/2014 | Bostrom | |
| 2014/0249479 A1 | 9/2014 | Pfrang | |
| 2014/0323985 A1 * | 10/2014 | Hourmand | A61M 5/24 604/232 |
| 2014/0330213 A1 * | 11/2014 | Hourmand | A61M 5/24 604/187 |
| 2014/0336590 A1 | 11/2014 | Hourmand et al. | |
| 2014/0350479 A1 | 11/2014 | Hourmand et al. | |
| 2016/0074584 A1 * | 3/2016 | Carmel | A61M 5/2033 604/218 |
| 2018/0064875 A1 | 3/2018 | Holmqvist | |
| 2018/0140781 A1 | 5/2018 | Kemp et al. | |
| 2019/0201629 A1 | 7/2019 | Hourmand et al. | |
| 2020/0405960 A1 | 12/2020 | Hourmand et al. | |
| 2020/0405961 A1 | 12/2020 | Hourmand et al. | |
| 2021/0077743 A1 | 3/2021 | Kemp et al. | |
| 2021/0346604 A1 | 11/2021 | Hourmand et al. | |
| 2022/0054755 A1 | 2/2022 | Hourmand et al. | |
| 2022/0054756 A1 | 2/2022 | Hourmand et al. | |
| 2022/0054757 A1 | 2/2022 | Hourmand et al. | |
| 2022/0054758 A1 | 2/2022 | Hourmand et al. | |
| 2024/0226441 A1 | 7/2024 | Hourmand et al. | |
| 2024/0238525 A1 | 7/2024 | Hourmand et al. | |
| 2024/0238526 A1 | 7/2024 | Hourmand et al. | |
| 2024/0238527 A1 | 7/2024 | Hourmand et al. | |
| 2024/0238528 A1 | 7/2024 | Hourmand et al. | |
| 2025/0001083 A1 | 1/2025 | Hourmand et al. | |
| 2025/0262389 A1 | 8/2025 | Kemp et al. | |

FOREIGN PATENT DOCUMENTS

| | | | |
|---|---|---|---|
| CN | 1911467 | 8/2006 | |
| CN | 2925504 | 7/2007 | |
| CN | 101400393 | 4/2009 | |
| CN | 101420995 | 4/2009 | |
| CN | 201213944 | 4/2009 | |
| CN | 103945879 | 7/2014 | |
| DE | 202009009119 | 12/2009 | |
| EA | 012008 | 6/2009 | |
| EA | 013934 | 8/2010 | |
| EP | 0518416 | 12/1992 | |
| EP | 0692272 | 1/1996 | |
| EP | 1702643 | 9/2006 | |
| EP | 2279771 | 2/2011 | |
| EP | 2438952 | 4/2012 | |
| EP | 2727617 | 6/2012 | |
| EP | 2601990 A1 * | 6/2013 | A61M 5/24 |
| EP | 2606925 A1 * | 6/2013 | A61M 5/2033 |
| EP | 2777684 | 9/2014 | |
| EP | 2788052 | 9/2015 | |
| FR | 2764195 | 12/1998 | |

| | | | |
|---|---|---|---|
| GB | 407109 | 3/1934 | |
| GB | 829724 | 3/1960 | |
| GB | 1122592 | 8/1968 | |
| GB | 2388033 | 11/2003 | |
| GB | 2396298 | 6/2004 | |
| GB | 2397767 | 8/2004 | |
| GB | 2447339 | 9/2008 | |
| GB | 2434317 | 1/2011 | |
| GB | 2471473 | 1/2011 | |
| JP | H08-10324 | 1/1996 | |
| JP | 2002-503127 | 1/2002 | |
| JP | 2005-021247 | 1/2005 | |
| JP | 2005-536300 | 12/2005 | |
| JP | 2006-507903 | 3/2006 | |
| JP | 2006-516901 | 7/2006 | |
| JP | 2008-500854 | 1/2008 | |
| JP | 2009-077943 | 4/2009 | |
| JP | 2009-523587 | 6/2009 | |
| JP | 2009-529395 | 8/2009 | |
| JP | 2014-500086 | 1/2014 | |
| JP | 2014-500089 | 1/2014 | |
| RU | 2068708 | 11/1996 | |
| RU | 2172638 | 8/2001 | |
| RU | 2311203 | 11/2007 | |
| RU | 2363500 | 8/2009 | |
| RU | 2012137269 | 3/2014 | |
| WO | WO 1998/035714 | 8/1998 | |
| WO | WO 1998/056442 | 12/1998 | |
| WO | WO 1999/010030 | 3/1999 | |
| WO | WO 1999/022792 | 5/1999 | |
| WO | WO 2000/024441 | 5/2000 | |
| WO | WO 2001/008727 | 2/2001 | |
| WO | WO 2001/060435 | 8/2001 | |
| WO | WO 2001/093926 | 12/2001 | |
| WO | WO 2002/047746 | 6/2002 | |
| WO | WO 2003/013632 | 2/2003 | |
| WO | WO 2003/068297 | 8/2003 | |
| WO | WO 2003/099358 | 12/2003 | |
| WO | WO 2004/007006 | 1/2004 | |
| WO | WO 2004/020026 | 3/2004 | |
| WO | WO 2004/050150 | 6/2004 | |
| WO | WO 2005/001161 | 1/2005 | |
| WO | WO 2013/083614 | 6/2005 | |
| WO | WO 2005/070481 | 8/2005 | |
| WO | WO 2005/083614 | 9/2005 | |
| WO | WO 2005/115506 | 12/2005 | |
| WO | WO 2005/115507 | 12/2005 | |
| WO | WO 2006/047810 | 5/2006 | |
| WO | WO 2006/085176 | 8/2006 | |
| WO | WO 2006/106291 | 10/2006 | |
| WO | WO 2006/106295 | 10/2006 | |
| WO | WO 2007/056792 | 5/2007 | |
| WO | WO 2007/083115 | 7/2007 | |
| WO | WO 2007/104636 | 9/2007 | |
| WO | WO 2007/129106 | 11/2007 | |
| WO | WO 2009/019437 | 2/2009 | |
| WO | WO 2009/022132 | 2/2009 | |
| WO | WO 2010/072644 | 7/2010 | |
| WO | WO 2010/097116 | 9/2010 | |
| WO | WO 2010/115822 | 10/2010 | |
| WO | WO 2010/136076 | 12/2010 | |
| WO | WO 2010/136078 | 12/2010 | |
| WO | WO 2010/147553 | 12/2010 | |
| WO | WO 2011/000570 | 1/2011 | |
| WO | WO 2011/001161 | 1/2011 | |
| WO | WO 2011/101378 | 8/2011 | |
| WO | WO 2012/073032 | 6/2012 | |
| WO | WO 2012/089445 | 7/2012 | |
| WO | WO 2012/164403 | 12/2012 | |
| WO | WO 2013/072182 | 5/2013 | |
| WO | WO 2021/008839 | 1/2021 | |

OTHER PUBLICATIONS

*SHL Medical AG* (Inventors: Anders Holmqvist, and Hsueh-Yi Chen) Junior Party (U.S. Appl. No. 17/020,027), v. *Sanofi-Aventis Deutschland GMBH* (Inventors: Yannick Hourmand, Douglas Ivan Jennings, and Matthew Ekman), Senior Party (U.S. Appl. No.

(56) References Cited

OTHER PUBLICATIONS

17/020,027), Patent Interference No. 106,135, Rough Transcript of Deposition of Gordon Row, dated May 6, 2022, 55 pages.
Brief Communication in European Opposition in Application No. 12795446.9, dated May 16, 2022, 15 pages.
Office Action in U.S. Appl. No. 16/871,897, dated May 18, 2022, 26 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Transcript of Deposition of Gordon Row, dated May 6, 2022, 61 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Reply 1, dated May 24, 2022, 34 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Reply 2, dated May 24, 2022, 35 pages.
Brief Communication in European Opposition in Application. No. 12795446.9, dated Jan. 5, 2023, 8 pages.
EP Observations by a Third Party in Patent Appln. No. 16195290.8, dated Aug. 24, 2021, 5 pages.
dictionary.com [online], "Circlip," 2016, retrieved on Feb. 24, 2022, retrieved from URL <https://www.dictionary.com/browse/circlip>, 4 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Decision on Priority, dated Aug. 22, 2023, 27 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Judgment, dated Aug. 22, 2023, 3 pages.
SHL Medical AG (Inventors: Anders Holmqvist, and Hsueh-Yi Chen) Junior Party (U.S. Appl. No. 17/020,027), v. Sanofi-Aventis Deutschland Gmbh (Inventors: Yannick Hourmand, Douglas Ivan Jennings, and Matthew Ekman), Senior Party (U.S. Appl. No. 17/020,027), Patent Interference No. 106,135, SHL Notice of Service of Supplemental Evidence, dated Jun. 7, 2022, 3 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Updated Exhibit List, dated Jun. 7, 2022, 4 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2025: Declaration of Neil Sheehan, dated Jun. 6, 2022, 9 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2001: Declaration of Neil Sheehan, dated Dec. 15, 2021, 44 pages.
Brief Communication in European Opposition in Application No. 12795446.9, dated Feb. 18, 2022, 34 pages.
Brief Communication in European Opposition in Application No. 12795446.9, dated Jan. 18, 2022, 57 pages.
Notice of Opposition in European Application No. 12795446.9, dated Aug. 19, 2021, 36 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2010—Merriam-Webster Definition of C-shaped, dated Jan. 10, 2021 , 2 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2023—Transcript of Videotaped Deposition of Nigel David Harrison, dated Feb. 18, 2022, 234 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2022: Declaration of Neil Sheehan, filed Apr. 6, 2022, 27 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1001—Declaration of Nigel David Harrison, dated Dec. 11, 2021, 19 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1013—Declaration of Gordon D. Row, MS, filed Apr. 7, 2022, 30 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1014—Transcript of Remote Deposition of Neil Sheehan taken Mar. 3, 2022, 105 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1015—Claim Chart demonstrating support for Sanofi's independent claim 2, filed Apr. 7, 2022, 11 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Medical Annotated Claims, filed Sep. 23, 2021, 9 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Medical Motion 2 (To Deny Benefit Accorded to Sanofi for Count 1), filed Dec. 15, 2021, 30 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Medical Motion 1 (For Judgment of No Written Description for Sanofi's Involved Claims), filed Dec. 15, 2021, 30 pages.

(56)     References Cited

OTHER PUBLICATIONS

*SHL Medical AG* (Inventors: Anders Holmqvist, and Hsueh-Yi Chen) Junior Party (U.S. Appl. No. 17/020,027) v. *Sanofi-Aventis Deutschland GMBH* (Inventors: Yannick Hourmand, Douglas Ivan Jennings, and Matthew Ekman), Senior Party (U.S. Appl. No. 17/020,027), Patent Interference No. 106,135, Shl Opposition 1, filed Apr. 7, 2022, 34 pages.

*SHL Medical AG* (Inventors: Anders Holmqvist, and Hsueh-Yi Chen) Junior Party (U.S. Appl. No. 17/020,027), v. *Sanofi-Aventis Deutschland GMBH* (Inventors: Yannick Hourmand, Douglas Ivan Jennings, and Matthew Ekman Senior Party (U.S. Appl. No. 17/020,027), Patent Interference No. 106,135, Sanofi Opposition 1 (Opposing SHL Motion 1 for Judgment for No Written Description), filed Apr. 7, 2022, 36 pages.

*SHL Medical AG* (Inventors: Anders Holmqvist, and Hsueh-Yi Chen) Junior Party (U.S. Appl. No. 17/020,027), v. *Sanofi-Aventis Deutschland GMBH* (Inventors: Yannick Hourmand, Douglas Ivan Jennings, and Matthew Ekman), Senior Party (U.S. Appl. No. 17/020,027), Patent Interference No. 106,135, Sanofi-Aventis Motion 1 For Judgment under for Lack of Written Description under Section 112, filed Dec. 15, 2021, 28 pages.

*SHL Medical AG* (Inventors: Anders Holmqvist, and Hsueh-Yi Chen) Junior Party (U.S. Appl. No. 17/020,027), v. *Sanofi-Aventis Deutschland GMBH* (Inventors: Yannick Hourmand, Douglas Ivan Jennings, and Matthew Ekman), Senior Party (U.S. Appl. No. 17/020,027), Patent Interference No. 106,135, Sanofi-Aventis Annotated Claims, filed Sep. 23, 2021, 7 pages.

*SHL Medical AG* (Inventors: Anders Holmqvist, and Hsueh-Yi Chen) Junior Party (U.S. Appl. No. 17/020,027), v. *Sanofi-Aventis Deutschland GMBH* (Inventors: Yannick Hourmand, Douglas Ivan Jennings, and Matthew Ekman), Senior Party (U.S. Appl. No. 17/020,027), Patent Interference No. 106,135, Sanofi Opposition 2 (Opposing SHL Motion 2 to Deny Benefit Accorded to Sanofi for Count 1), filed Apr. 7, 2022, 38 pages.

Interlocutory decision in Opposition proceedings in European Appln. No. 12795446.9, dated Mar. 31, 2023, 52 pages.

*Anders Holmqqvist*, and *Hsueh-Yi Chen*, Junior Party (U.S. Appl. No. 17/020,027) v. *Yannick Hourmand, Douglas Ivan Jennings*, and *Matthew Ekman*, Senior Party (U.S. Appl. No. 17/020,027), Declaration of Interference, Patent Interference No. 106,135, filed Aug. 26, 2021, 8 pages.

CN Search Report in Chinese Appln. 201280069195.4, dated Dec. 5, 2012, 2 pages (with English translation).

CN Search Report in Chinese Appln. 201280069203.5, dated Oct. 9, 2015, 2 pages (with English translation).

EP Extended Search Report in European Appln. 16195290.8, dated Mar. 15, 2017, 6 pages.

EP Extended Search Report in European Appln. 16195292.4, dated Mar. 17, 2015, 6 pages.

EP Search Report in European Appln. 11192585.5, dated Apr. 20, 2012, 5 pages.

Merriamebster.com [online], "Hinge," Retrieved on Dec. 18, 2016, retrieved from URL <https://www.merriamwebster.com/dictionary/hinge>, 14 pages.

PCT International Preliminary Report on Patentability in International Appln No. PCT/EP2016/062462, dated Dec. 5, 2017, 7 pages.

PCT International Preliminary Report on Patentability in International Appln. No. PCT/EP2012/074466, dated Jun. 10, 2014, 5 pages.

PCT International Preliminary Report on Patentability in International Appln. No. PCT/EP2012/074468, dated Jun. 10, 2014, 5 pages.

PCT International Preliminary Report on Patentability in International Appln. No. PCT/EP2012/074469, dated Jun. 10, 2014, 5 pages.

PCT International Preliminary Report on Patentability in International Appln. No. PCT/EP2012/074471, dated Jun. 10, 2014, 6 pages.

PCT International Preliminary Report on Patentability in International Appln. No. PCT/EP2016/062503, dated Dec. 5, 2017, 6 pages.

PCT International Search Report and Written Opinion in International Appln. No. PCT/EP2012/074466, dated Feb. 7, 2013, 9 pages.

PCT International Search Report and Written Opinion in International Appln. No. PCT/EP2012/074468, dated Mar. 13, 2013, 7 pages.

PCT International Search Report and Written Opinion in International Appln. No. PCT/EP2012/074469, dated Feb. 26, 2013, 7 pages.

PCT International Search Report and Written Opinion in International Appln. No. PCT/EP2012/074471, dated Mar. 22, 2013, 8 pages.

PCT International Search Report and Written Opinion in International Appln. No. PCT/EP2016/062462, dated Sep. 27, 2016, 10 pages.

PCT International Search Report and Written Opinion in International Appln. No. PCT/EP2016/062503, dated Aug. 17, 2016, 9 pages.

PCT International Search Report and Written Opinion in International Appln. No. PCT/GB2005/002108, dated Sep. 6, 2005, 2 pages.

PCT International Search Report in International Appln. No. PCT/EP2011/052300, dated Jun. 16, 2011, 4 pages.

PCT International Search Report in International Appln. No. PCT/US00/20623, dated Nov. 21, 2000, 3 pages.

Merriam-webster.com [online], "Clamp," May 27, 2006, retrieved on Jun. 21, 2024, retrieved from URL <https://www.merriam-webster.com/dictionary/clamp#:~:text=Synonyms%20of%20clamp-,1,for%20holding%20or%20compressing%20something>, 1 page.

Notice of Opposition filed by Ypsomed AG in European Application No. 16195290.8, dated Oct. 10, 2023, 24 pages.

Notice of Opposition filed by Barker Brettell LLP in European Application No. 16195290.8, dated Oct. 11, 2023, 41 pages.

* cited by examiner

AUTOINJECTOR AND METHOD OF ASSEMBLING

CROSS REFERENCE TO RELATED APPLICATIONS

The present application is a continuation of U.S. patent application Ser. No. 15/579,024, filed on Dec. 1, 2017, which is the national stage entry of International Patent Application No. PCT/EP2016/062462, filed on Jun. 2, 2016, and claims priority to Application No. EP 15170597.7, filed on Jun. 3, 2015, the disclosures of which are expressly incorporated herein in entirety by reference thereto.

TECHNICAL FIELD

The disclosure relates to an autoinjector and method of assembling the autoinjector.

BACKGROUND

Administering an injection is a process that presents a number of mental and physical risks and challenges for users and healthcare professionals. Injection devices typically fall into two categories—manual devices and autoinjectors. In a conventional manual device, manual force is required to drive a medicament through a needle. This is typically done by a plunger, which is continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). Additionally, aligning the injection device, administering the injection, and keeping the injection device still during the injection, may require dexterity which some patients may not have.

Autoinjector devices aim to make self-injection easier for patients. A conventional autoinjector may provide the force for administering the injection by a spring, a trigger button, or other mechanisms used to activate the injection. Autoinjectors may be single-use or reusable devices.

SUMMARY

According to aspects of the current disclosure, there is provided a syringe carrier for an autoinjector comprising a housing adapted to receive a syringe having a needle encapsulated by a removable protective needle sheath, and two or more flexible arms protruding outwards in a relaxed state and adapted to couple with the syringe in a mounted position, wherein in the mounted position, the flexible arms are deflected radially inwards due, in part, to an axial force operating on the syringe carrier.

The flexible arms are deflected radially inwards due to a relative movement of the syringe carrier with respect to the syringe. This relative movement may be caused by the axial force on the syringe carrier. The inward deflection of the flexible arms is provided by a ramp control. For example, the case comprises a ramp at its inner surface.

In an exemplary embodiment, the flexible arms extend distally from a carrier front end. In a further exemplary embodiment, the flexible arms are symmetrically arranged around the carrier front end. The flexible arms protrude radially outwards in a relaxed state.

In an exemplary embodiment, the flexible arms, in particular a distal end of the flexible arms comprise protrusions inwardly directed onto the syringe and configured to couple with a distal shoulder of the syringe. Preferably, the syringe is a pre-filled syringe having a needle. Alternatively, a medicament container having a needle may be provided.

According to a further embodiment, an outer diameter of the protrusions is smaller than an outer diameter of the protective needle sheath and an outer diameter of a shaft of the syringe. The smaller outer diameter of the protrusions supports and thus pre-positions the syringe at an axial position with respect to the syringe carrier and the protective needle sheath in the final mounted position.

In an exemplary embodiment, the housing includes a proximal aperture having an outer diameter, in part, smaller than an outer diameter of a proximal syringe flange. When moving the syringe within the syringe carrier, the proximal syringe flange engages and rests onto a carrier rear end of the proximal aperture. Preferably, the proximal aperture has an elliptical or oval form and thus the outer diameter of the proximal aperture may be smaller as well as larger than the circular outer diameter of the proximal syringe flange.

According to another aspect of the current disclosure, there is provided an autoinjector comprising at least a syringe carrier and a case adapted to receive the syringe carrier.

In an exemplary embodiment, the case is adapted to inwardly deflect the flexible arms in the mounted position when the axial force operates onto the syringe carrier. In an exemplary embodiment, the case comprises at least one inwardly directed edge, e.g. a ramp, operating onto the flexible arms wherein the inward deflection of the flexible arms in the mounted position forces the syringe and the protective needle sheath apart when the axial force operates onto the syringe carrier. The design of the syringe carrier and the case are such that a protective needle sheath, e.g. a rigid or a rubber needle sheath, is automatically displaced to a predetermined position during assembly to provide sufficient clearance to support the syringe at the datum.

In an exemplary embodiment, the case comprises at least one inwardly directed rigid edge, e.g. circumferential-ridged edge or latches, at a distal end in the direction of the protective needle sheath. In another embodiment, the edge is formed as a ramp.

In an exemplary embodiment, the syringe carrier comprises holding clamps on an axial carrier rear end, e.g. opposite to the direction of the protective needle sheath for releasable holding of the syringe carrier in the case. The holding clamps are integrally formed with the syringe carrier, e.g. as tongues. In particular, the holding clamps are outwardly directed. Furthermore, the syringe carrier comprises at least two clamps arranged opposite to each other on a carrier rear end, e.g. on a carrier flange or carrier head.

In an exemplary embodiment, the case comprises at least one inner support to releasably hold the holding clamps. In particular, the inner support may be formed as an inner groove or slot or opening.

In an exemplary embodiment, the case comprises a front case and a rear case.

The front case may be adapted to releasably hold the carrier at its rear end and to fixedly hold the carrier at its front end. Furthermore, the front case is adapted to enclose the autoinjector and to deflect the flexible arms of the carrier radially inwards in the mounted position.

Furthermore, the rear case is adapted to prevent axial movement of the syringe relative to the case and to close an axial case end opposite to the direction of the protective needle sheath.

In an exemplary embodiment, the autoinjector further comprises a needle shroud telescopically coupled to the case and movable between an extended position relative to the case in which the needle is covered and a retracted position relative to the case in which the needle is exposed, a shroud spring biasing the needle shroud in a distal direction relative to the case, a plunger slidably disposed in the case, and a drive spring to drive the plunger.

In an exemplary embodiment, the case comprises the front case and the rear case which is surrounded by the front case along a longitudinal direction and adapted to close an open proximal end of the front case.

In an exemplary embodiment, the needle shroud includes an inner shroud boss on which an inner case boss of the case abuts.

In an exemplary embodiment, due to an axial force applied to the rear end of the syringe carrier, the holding clamps are released from the case so that the syringe carrier together with the assembled syringe may be moved within the case.

In an exemplary embodiment, the case comprises one or more openings or one or more apertures to allow insertion of at least one assembling tool for applying a force to release the at least one holding clamp of the syringe carrier from the case and to move the syringe carrier within the case.

According to a further aspect of the current disclosure, a method of assembling an autoinjector is provided and comprises the steps of: providing a case in which a syringe carrier with flexible arms protruding inwards in a relaxed state is mounted, providing a syringe with a needle encapsulated by a removable protective needle sheath, inserting and pre-positioning the syringe axially into the syringe carrier and inserting a front-assembling tool at a distal end of the case and a back-assembling tool at a proximal end of the case, finally mounting the syringe into the syringe carrier by releasing the syringe carrier from the case and moving the syringe carrier forwards within the case until the flexible arms are deflected radially inwards to couple with the syringe in the mounted position due, in part, to an axial force operating on the syringe carrier.

The inward deflection of the flexible arms in the mounted and final position displaces the protective needle sheath to allow space to support the syringe at its datum. In this mounted position, the flexible arms of the syringe carrier are held rigidly by the case, e.g. by a ramp or edge, and thus safely support the syringe.

The flexible arms radially deflect due, in part, to an axial force operating on the syringe carrier, so that the syringe carrier is relatively moved with respect to the case and, finally, in addition with respect to the syringe.

In an exemplary embodiment, for inserting the syringe into the syringe carrier, the syringe is moved into an opened carrier rear end axially forwards until a syringe flange engages the carrier rear end.

When inserting the syringe into the syringe carrier, for example, a back-assembling tool is pushed axially forward onto the syringe.

In an exemplary embodiment, for releasing the syringe carrier from the case and moving the syringe carrier forwards within in the case, for example, a back-assembling tool is pushed axially forward onto the syringe carrier so that the carrier moves together with the syringe in a forward direction.

For finally mounting and positioning of the syringe within the syringe carrier, when moving the syringe carrier forwards within the case and reaching the mounted position, the syringe carrier with the syringe is moved forwards until the protective needle sheath of the syringe engages and comes in contact with the front-assembling tool arranged in the cap so that the syringe stops and is fixed. The back-assembling tool keeps pushing on the syringe carrier. Due to these further axial forces onto the syringe carrier, the syringe carrier is further relatively moved with respect to the syringe until the syringe carrier contacts the front-assembling tool arranged in the cap. At this point, the flexible arms engage a case ramp or case edge so that the flexible arms slide over the ramp or edge and are deflected radially inwards when reaching the final mounted position. In this final mounted position, the flexible arms engage and displace the protective needle sheath to allow space to support the syringe in its final position and at its datum. Further, in this final mounted position, the case is adapted to restrain and support the inward deflection of the flexible arms, forcing the syringe and the protective needle sheath apart.

According to a further aspect of the current disclosure, a method of assembling an autoinjector is provided and comprises the steps of: providing a front subassembly comprising a front case with a mounted needle shroud and an open case rear end in which the syringe carrier with a carrier front end and a carrier rear end is mounted, providing the syringe with a needle encapsulated by a removable protective needle sheath, inserting the syringe axially into the case rear end by pushing a syringe flange until the syringe flange engages the carrier rear end, finally mounting the syringe into the carrier by the following steps: releasing the syringe carrier from the case and moving the syringe carrier forwards, so that the syringe carrier together with the syringe moves in a forward direction within the case until the flexible arms are deflected radially inwards to couple with the syringe in the mounted position due, in part, to an axial force operating on the syringe carrier.

The case is adapted to restrain the inward deflection of the flexible arms when the syringe carrier reaches the mounted position such that, due to an axial force acting onto the syringe carrier, the case operates onto the flexible arms, forcing the syringe and the protective needle sheath apart. The flexible arms engage behind the rear end of the protective needle sheath. The protective needle sheath and the syringe are spaced apart until the flexible arms are restrained and forced radially inwards by the case. At this point, the syringe carrier and the protective needle sheath move as one while the syringe is "left behind" until the flexible arms of the syringe carrier are fully engaged.

The carrier design allows accurate support of the syringe on its datum despite large variations in syringe and needle shield dimensions and in the relative positioning of the needle shield and syringe. In particular, the syringe carrier, namely the inwardly deflected arms, allows a large syringe datum with a robust support surface with high safety margin. Furthermore, the final assembling is simplified and allows an axial assembly process.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description. The present invention will become more fully understood from the detailed description given hereinbelow and the accompanying drawings which are given by way of illustration only, and thus, are not limitive of the present invention.

BRIEF DESCRIPTION OF THE FIGURES

Corresponding parts are marked with the same reference symbols in all figures.

DETAILED DESCRIPTION

Figure 1:
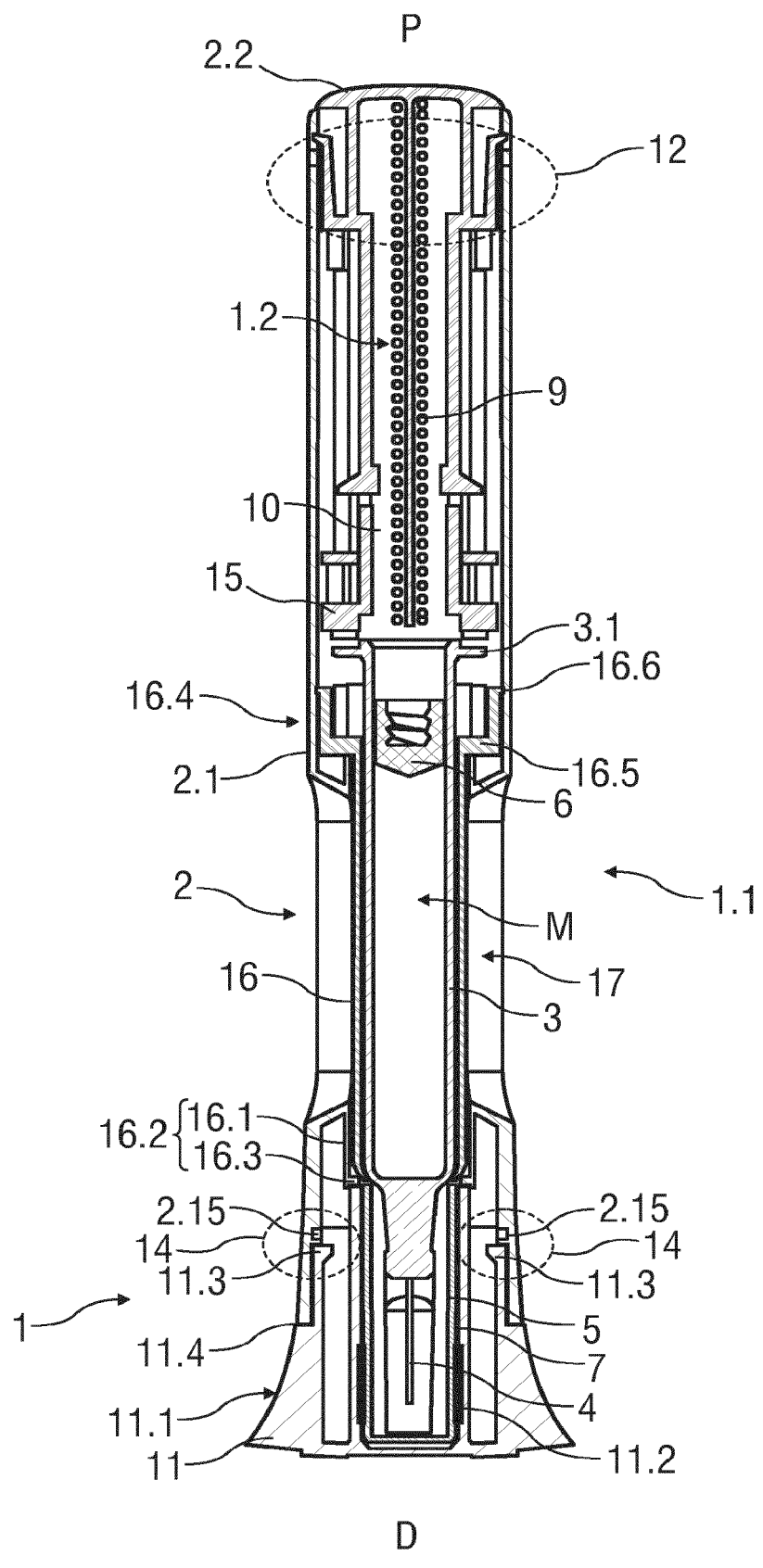
FIG. 1 is a simplified longitudinal section of an exemplary embodiment of an autoinjector after assembly.
Figure 2A:
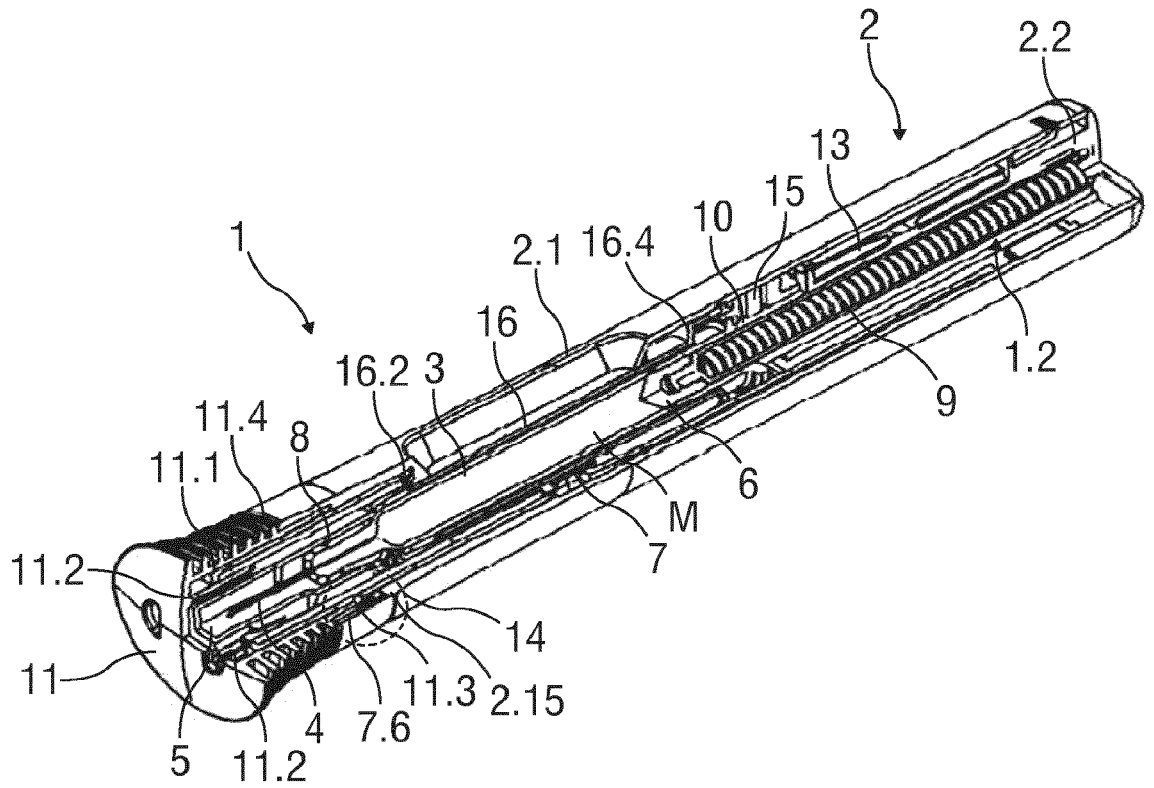
FIGS. 2A to 2D are schematic perspective partly cut-away views after assembly (in more detail), an explosion view of an exemplary embodiment of an autoinjector, a perspective view of an exemplary embodiment of a back-assembling tool and a perspective view of an exemplary embodiment of a front-assembling tool.
Figure 2B:
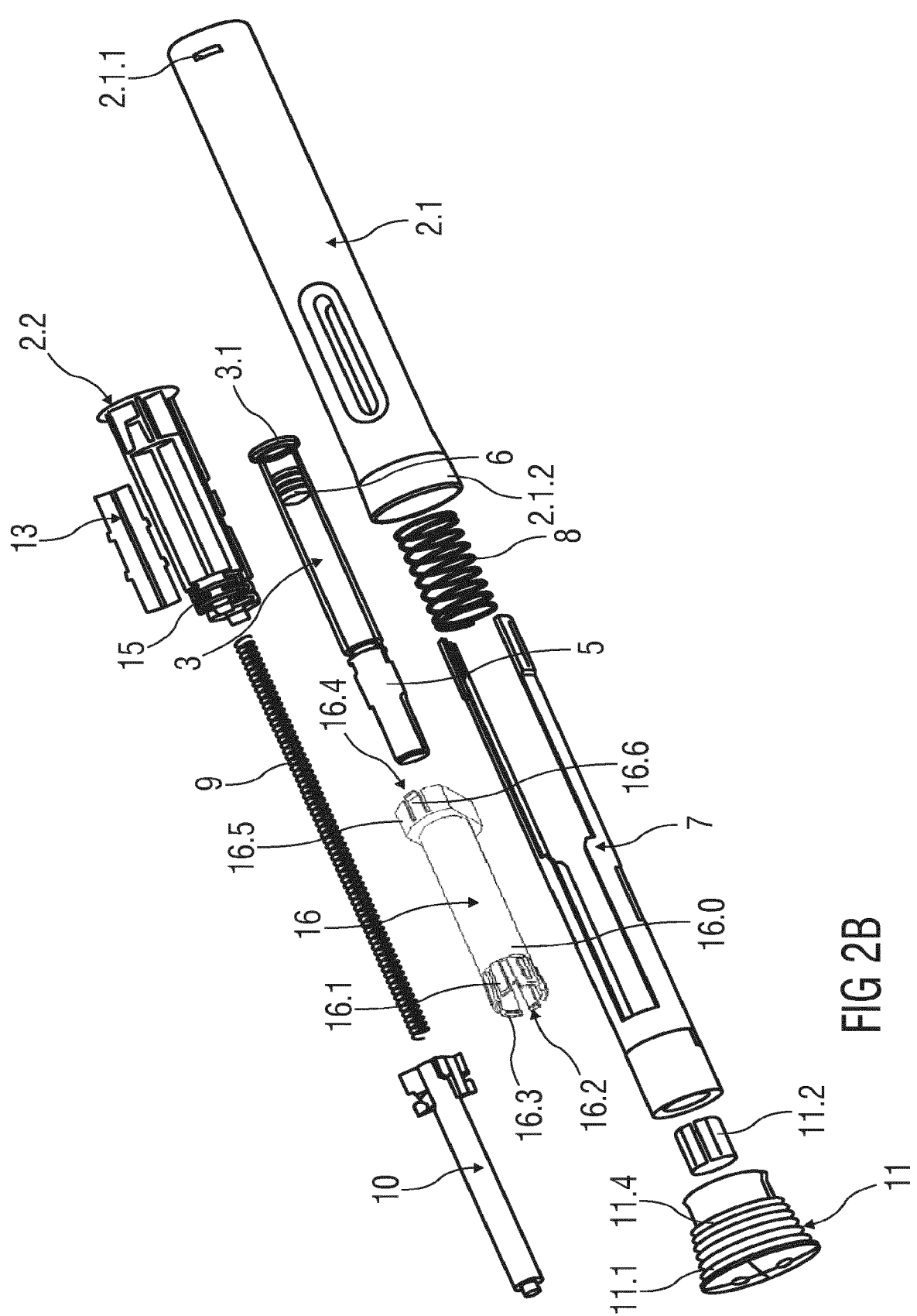

FIG. 1 is a simplified longitudinal section of an exemplary embodiment of an autoinjector 1 after assembly and shows the main assembling parts. FIG. 2A is a schematic perspective partly cut-away view of the autoinjector 1. FIG. 2B shows an explosion view of all components of the autoinjector 1. FIGS. 2A, 2B show the assembled autoinjector 1 in more detail.

The autoinjector 1 comprises a case 2. The case 2 is designed as a multi-part. In particular, the case 2 comprises a front case 2.1 and a rear case 2.2. The rear case 2.2 is surrounded by the front case 2.1 along a longitudinal direction and adapted to close an open proximal end of the front case 2.1. The case 2 is adapted to hold a syringe 3.

The syringe 3 may be a pre-filled syringe or a pre-filled medicament container and has a needle 4 arranged at a distal end. The syringe 3 may be pre-assembled. Typically, a protective needle sheath 5 may be removably coupled to the needle 4. The protective needle sheath 5 may be a rubber needle sheath or a rigid needle sheath (which is composed of rubber and a full or partial plastic shell).

A stopper 6 is arranged for sealing the syringe 3 proximally and for displacing a medicament M contained in the syringe 3 through the needle 4. In other exemplary embodiments, the syringe may be a cartridge or a container which includes the medicament M and engages a removable needle (e.g., by threads, snaps, friction, etc.).

In an exemplary embodiment, a cap 11 may be removably disposed at a distal end of the case 2. The cap 11 may include a grip element 11.2 (e.g., a barb, a hook, a narrowed section, etc.) arranged to engage the protective needle sheath 5, the cap 11 and/or a needle shroud 7 telescoped within the case 2. The cap 11 may comprise grip features 11.1 for facilitating removal of the cap 11 (e.g., by twisting and/or pulling the cap 11 relative to the case 2.

Furthermore, the cap 11 comprises a barb 20 grasping the protective needle sheath 5 in a final mounted position of the syringe 3 within the case 2.

In an exemplary embodiment, a shroud spring 8 (shown in FIG. 2A) is arranged to bias the needle shroud 7 in a distal direction D against the case 2.

In an exemplary embodiment, a drive spring 9 is arranged within the case 2. A plunger 10 serves for forwarding a force of the drive spring 9 to the stopper 6. In an exemplary embodiment, the plunger 10 is hollow and the drive spring 9 is arranged within the plunger 10 biasing the plunger 10 in the distal direction D against the case 2. In another exemplary embodiment, the plunger 10 may be solid and the drive spring 9 may engage a proximal end of the plunger 10. Likewise, the drive spring 9 could be wrapped around the outer diameter of the plunger 10 and extend within the syringe 3.

In an exemplary embodiment, a plunger release mechanism 12 is arranged for preventing release of the plunger 10 prior to retraction of the needle shroud 7 relative to the case 2, and for releasing the plunger 10 once the needle shroud 7 is sufficiently retracted.

In an exemplary embodiment, a shroud lock mechanism 14 is arranged to prevent retraction of the needle shroud 7 relative to the case 2 when the cap 11 is in place, thereby avoiding unintentional activation of the autoinjector 1 (e.g., if dropped, during shipping or packaging, etc.).

The shroud lock mechanism 14 may comprise one or more compliant beams 11.3 on the cap 11 and a respective number of apertures 7.6 (shown in FIG. 2A) in the needle shroud 7 adapted to receive each of the compliant beams 11.3. When the cap 11 is attached to the autoinjector 1, the compliant beams 11.3 abut a radial stop 2.15 on the case 2, which prevents the compliant beams 11.3 from disengaging the apertures 7.6.

When the cap 11 is attached to the autoinjector 1, axial movement of the cap 11 in the proximal direction P relative the case 2, is limited by a rib 11.4 on the cap 11 abutting the case 2. When the cap 11 is pulled in the distal direction D relative to the case 2, the compliant beams 11.3 may abut an edge of the aperture 7.6 and deflect to disengage the aperture 7.6, allowing for removal of the cap 11 and the protective needle sheath 5 attached thereto.

Figure 2C:
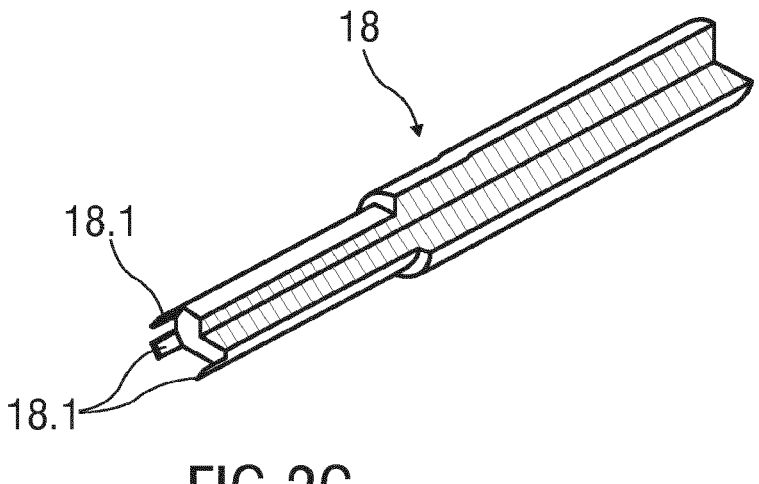
Figure 2D:
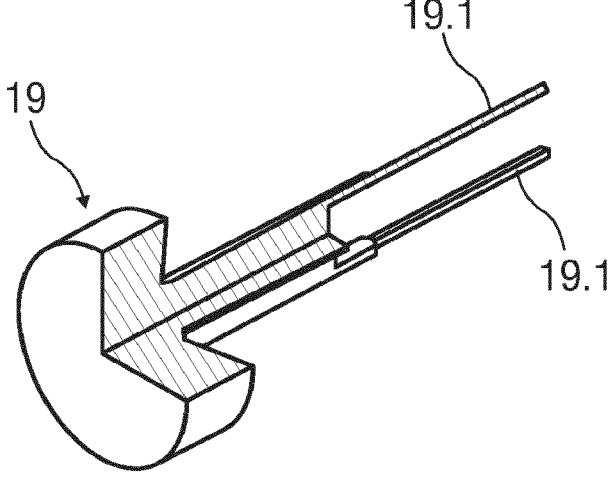

In the shown embodiment, the cap 11 comprises a closable opening 11.5 for inserting a front assembling tool 19 (an example is shown in FIG. 2D).

In an exemplary embodiment, the compliant beams 11.3 and/or the apertures 7.6 may be ramped to reduce force necessary to disengage the compliant beams 11.3 from the apertures 7.6.

The autoinjector 1 comprises at least an audible indicator 13 (shown in FIG. 2A) for producing an audible feedback of completion of medicament M delivery. The audible indicator 13 is formed, for example, as a bistable spring and is held in the rear case 2.2.

The rear case 2.2 is adapted to prevent axial movement of the syringe 3 after assembling, in particular during storage, transportation, and normal use. In detail, the rear case 2.2 comprises at its front end resilient arms 15. The resilient arms 15 are formed as inwardly directed arms in a relaxed state.

To allow an accurate support of the syringe 3 during and after assembling, the autoinjector 1 comprises a syringe carrier 16. The syringe carrier 16 is adapted to assemble and hold the syringe 3 within the case 2 and is further explained in more detail.

In particular, the syringe 3 is a 1.0 ml pre-filled syringe with a rigid protective needle sheath 5. Usually, the syringe 3 and the protective needle sheath 5 have large variations in dimensions. To allow accurate support of the syringe 3 in a mounted position despite these large variations, the design of the syringe carrier 16 and the front case 2.1 are adapted to automatically displace and position the protective needle sheath 5 to a predetermined position during assembly to provide sufficient clearance to support the syringe 3 at its datum in the mounted position.

Therefore, the syringe carrier 16 comprises flexible arms 16.1 adapted to mount and position the syringe 3 and hold it in a mounted position. The flexible arms 16.1 protrude outwards in a relaxed state.

The syringe carrier 16 comprises a housing 16.0 adapted to receive the syringe 3 and at least two flexible arms 16.1 adapted to couple with the syringe 3 in the mounted position. The housing 16.0 is formed as a hollow cylinder.

he flexible arms 16.1 are distally extended from an axial carrier front end 16.2 of the housing 16.0. The flexible arms 16.1 protrude outwards in a relaxed state, e.g. are outwardly formed, e.g. angled. The flexible arms 16.1 comprise inwardly directed protrusions 16.3 at distal ends of the flexible arms 16.1.

To support the final assembly of the syringe 3 into the syringe carrier 16, the at least two flexible arms 16.1 are adapted to couple with the syringe 3 in the mounted position, such that the outwardly protruded flexible arms 16.1 are deflected radially inwards in the mounted position due to a relative movement of the syringe carrier 16 with respect to the syringe 3. This relative movement may be caused by an axial force operating on the syringe carrier 16, e.g. on a carrier rear end 16.4.

Furthermore, the front case 2.1 is adapted to restrain the inward deflection of the flexible arms 16.1 when the syringe 3 is in the mounted position, such that an assembled force of the case 2 operates onto the flexible arms 16.1, forcing the syringe 3 and the protective needle sheath 5 apart, so that the syringe 3 is secured in the mounted position shown in FIGS. 1 and 2A.

The carrier 16 comprises a carrier rear end 16.4 opposite to the carrier front end 16.2. At the carrier rear end 16.4, the carrier 16 comprises a carrier flange 16.5 with holding clamps 16.6 for releasable intermittent holding of the carrier 16 relative to the case 2.

The holding clamps 16.6 are integrally formed on the carrier flange 16.5 as tongues. Proximal ends of the holding clamps 16.6 are outwardly directed to engage slots 2.1.1 of the case 2. In an embodiment, the carrier 16 comprises two holding clamps 16.6 arranged opposite to each other.

Instead of slots 2.1.1, the front case 2.1 may comprise an inner support to releasably hold the holding clamps 16.6. In particular, the inner support may be formed as an inner groove.

Furthermore, the syringe carrier 16 comprises ribs 16.8 on the outer surface of the flexible arms 16.1 to provide a stopping function for the relative movement of the syringe carrier 16 with respect to the syringe 3. The ribs 16.8 correspond with cuts or nuts (not shown) within the inner surface of the front case 2.1.

In an exemplary embodiment, the autoinjector 1 may be formed from at least two subassemblies, e.g., a control or front subassembly 1.1 and a drive or rear subassembly 1.2, to allow for flexibility as to the time and location of manufacture of the subassemblies 1.1, 1.2 and final assembly with the syringe 3.

FIGS. 2C and 2D show a perspective view of an exemplary embodiment of a back-assembling tool 18 having rigid arms 18.1 and of a front-assembling tool 19 having rigid arms 19.1.

Figure 3:
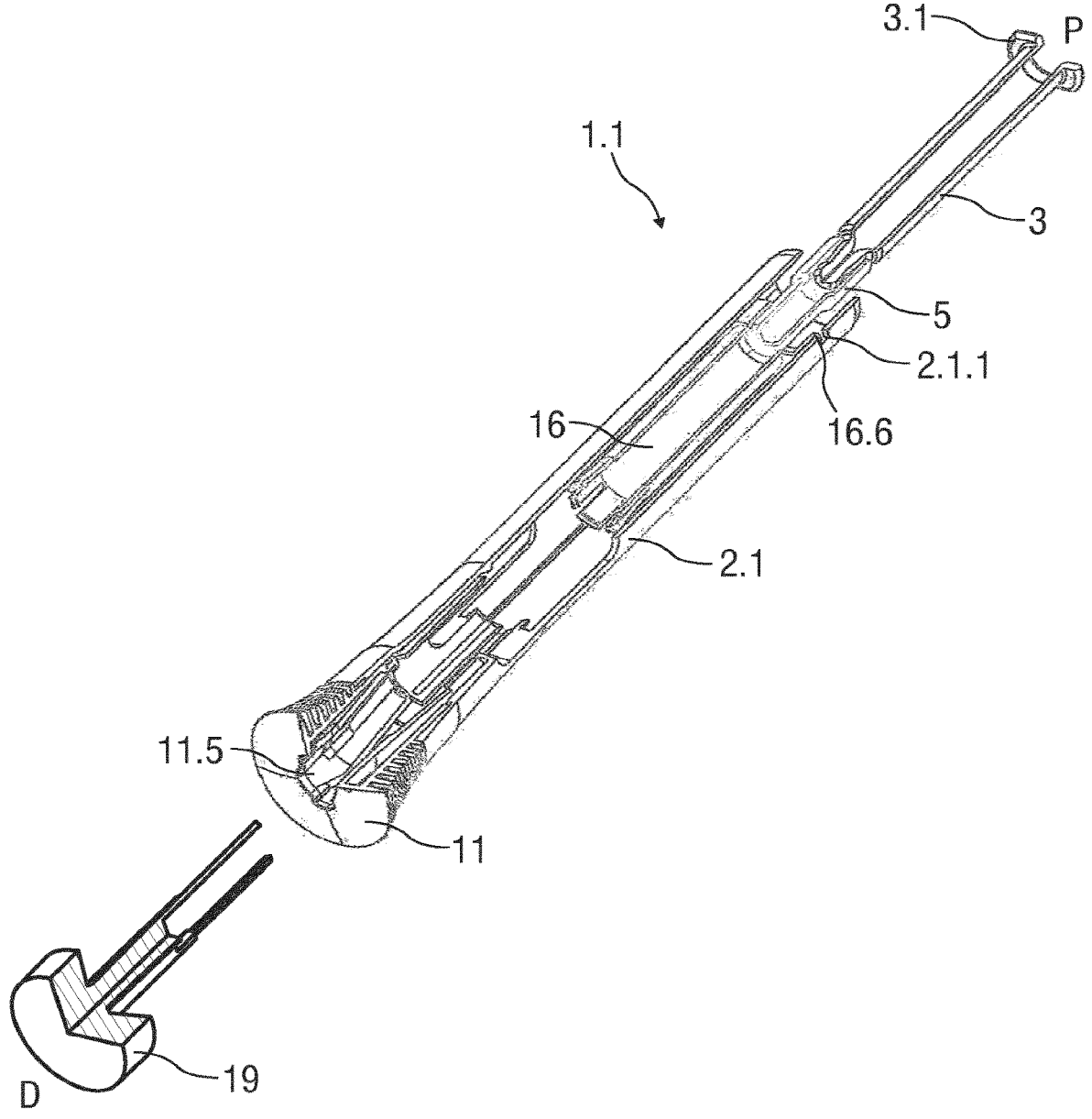
FIG. 3 is a schematic exploded view of an exemplary embodiment of a front subassembly comprising a front case with a mounted syringe carrier into which a syringe is to be assembled and of a front-assembling tool.

FIG. 3 is a perspective exploded view of an exemplary embodiment of a front subassembly 1.1 of an autoinjector 1.

In an exemplary embodiment, the front subassembly 1.1 comprises at least the front case 2.1, the needle shroud 7 and the syringe carrier 16, in which the syringe 3 is assembled.

The needle shroud 7 and the syringe carrier 16 are mounted into the front case 2.1. In particular, the syringe carrier 16 is stable due to clamp connection of the holding clamps 16.6 within slots 2.1.1 of the front case 2.1 at its rear end.

For assembling the syringe 3 into the syringe carrier 16 and thus into the front case 2.1, the case 2 comprises one or more apertures to allow insertion of the syringe 3 and insertion of the front-assembling tool 19.

As shown in FIG. 3, the case 2, in particular the front case 2.1, is provided in which the syringe carrier 16 is pre-assembled and mounted. The syringe 3 with the needle 4 encapsulated by the removable protective needle sheath 5 is inserted and pre-positioned axially into the syringe carrier 16 as described in more detail below.

To assemble the front subassembly 1.1, the syringe carrier 16 is axially inserted into the front case 2.1 from a proximal end P, until holding clamps 16.6 of the syringe carrier 16 engage retaining slots 2.1.1 in the front case 2.1, so that the syringe carrier 16 is fixed and stable in the front case 2.1.

Additionally, the shroud spring 8 is inserted into the needle shroud 7 (shown in FIG. 1, not shown in FIG. 4) and the needle shroud 7 with the shroud spring 8 is inserted into a distal end 2.1.2 of the front case 2.1. The cap 11 together with the barb 11.2 is arranged over the distal end of the needle shroud 7.

Figures 4, 5:
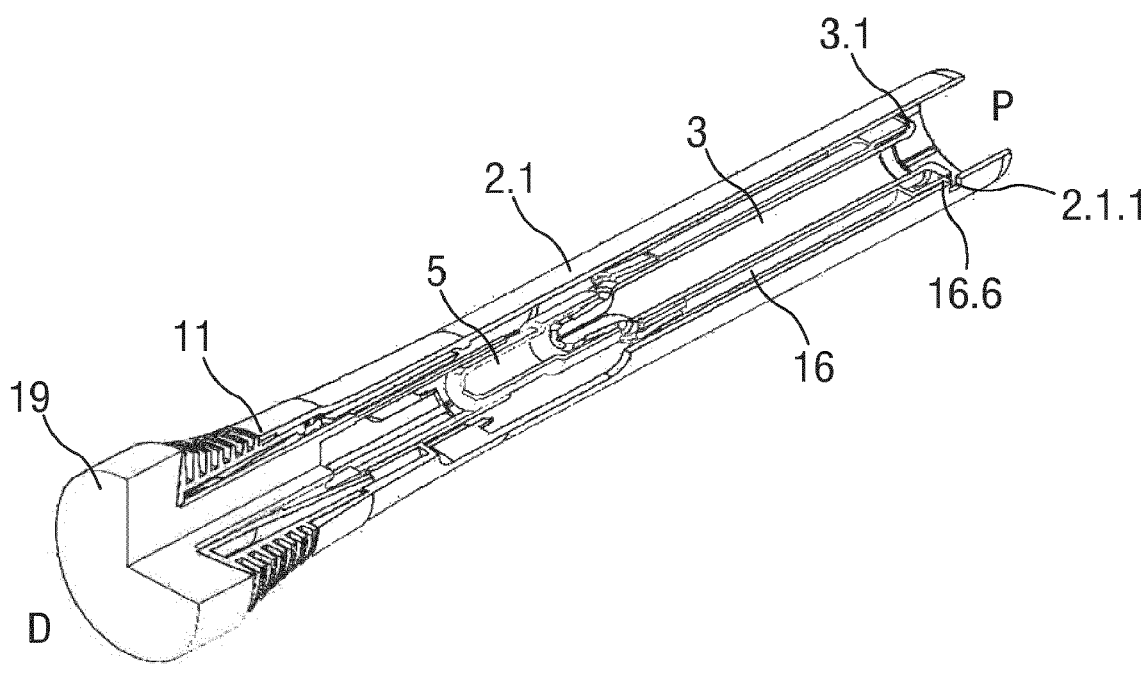
FIG. 4 is a schematic perspective view of an exemplary embodiment of a front subassembly with a mounted front case into which a syringe and a front-assembling tool are mounted.
FIG. 5 is a schematic enlarged partial view of the rear end of the front subassembly.

After the syringe carrier 16 is fixed in the front case 2.1, the syringe 3 may be inserted into the front subassembly 1.1, namely into the syringe carrier 16 from its carrier rear end 16.4. In particular, the syringe 3 is dropped into the opened carrier rear end 16.4 axially forwards until the syringe flange 3.1 engages the carrier rear end 16.4 as it is shown in FIGS. 4 and 5. In particular, the syringe flange 3.1 engages a proximal shoulder 16.5.1 of the carrier flange 16.5. Alternatively, the syringe flange 3.1 engages a distal shoulder of the carrier flange 16.5.

When inserting the syringe 3 into the syringe carrier 16, the front-assembling tool 19 is inserted into the front case 2.1. In particular, the front-assembling tool 19 is pushed into the cap 11 and onto the protective needle sheath 5 axially forwards.

When the syringe 3 is inserted into the syringe carrier 16, the flexible arms 16.1 protrude outwards and engage a shaft of the syringe 3 (shown in FIG. 4).

FIG. 4 shows in detail the front subassembly 1.1 with the mounted syringe carrier 16 together with the mounted syringe 3 in an intermediate assembling position.

As the protective needle sheath 5 is usually larger than the syringe diameter, the syringe 3 cannot be assembled into the front case 2.1 through the needle shroud 7. To overcome this problem, the syringe carrier 16 is provided. Hence the housing 16.0 of the syringe carrier 16 comprises an inner diameter larger than the outer diameter of a shaft of the syringe 3. Furthermore, the housing 16.0 includes a proximal aperture having an outer diameter, in part, smaller than an outer diameter of the proximal syringe flange 3.1.

In this corresponding intermediate assembling position of the front subassembly 1.1 with the assembled syringe carrier 16 and the syringe 3, the holding clamps 16.6 are held in the slots 2.1.1 and the flexible arms 16.1 of the syringe carrier 16 outwardly deflect and sit on the barrel or shaft of the syringe 3.

Figure 6A:
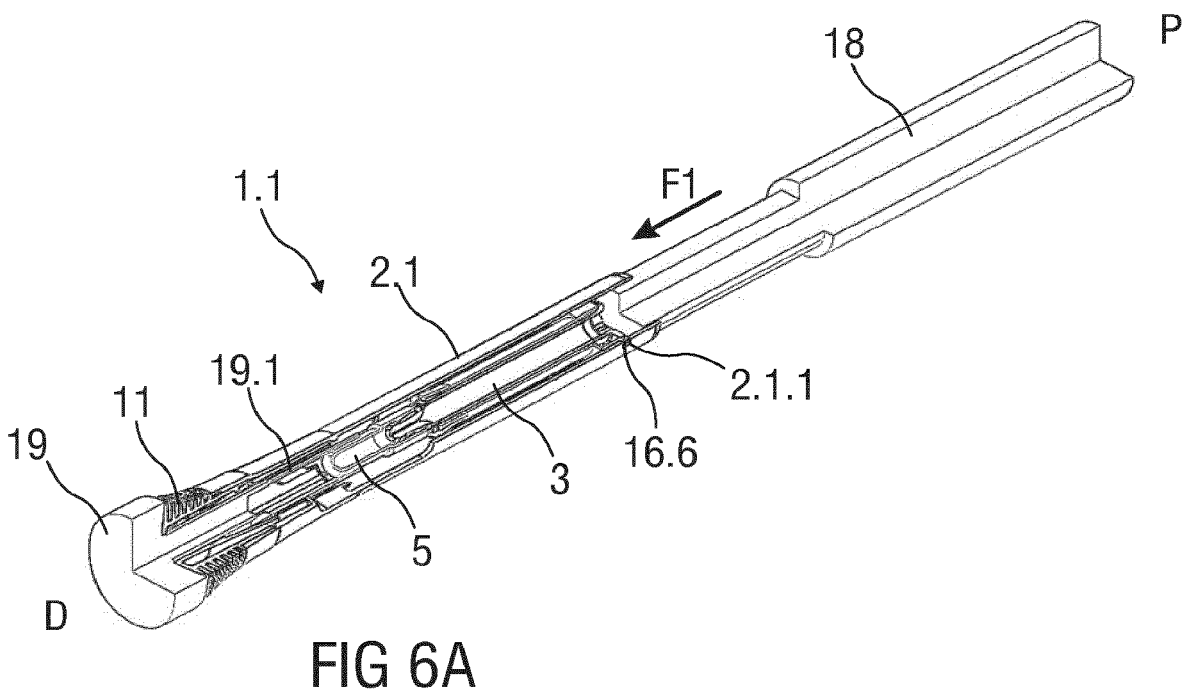
FIGS. 6A, 6B, 6C are schematic perspective views of an exemplary embodiment of a front subassembly with a mounted front case into which a front-assembling tool and a back-assembling tool are mounted.
Figure 6B:
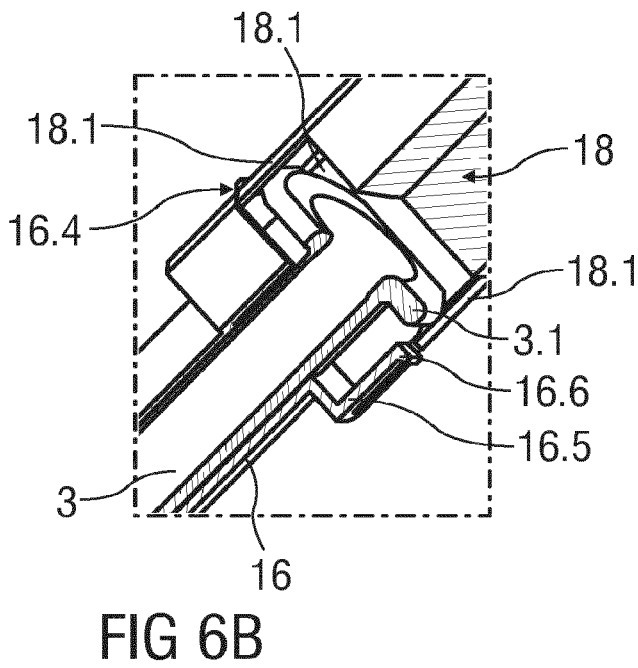
Figure 6C:
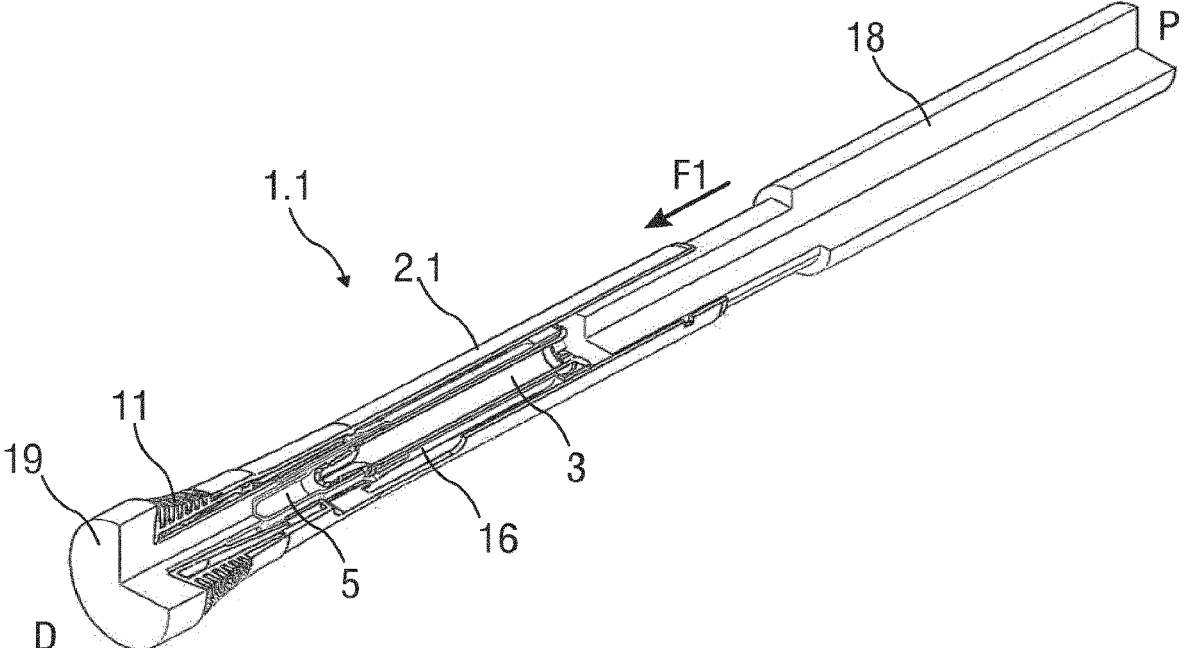

As it is shown in FIGS. 6A to 6C, afterwards, for final positioning of the syringe 3 within the syringe carrier 16, an axial force according to arrow Fl is then applied to the syringe carrier 16 so that the holding clamps 16.6 are released from the slots 2.1.1 and the syringe carrier 16 together with the syringe 3 is moved within the case 2 into the distal direction D.

The axial force F1 applied to the syringe carrier 16 is smaller than a holding force, e.g. friction force, between the syringe carrier 16 and the syringe 3, e.g. between their contacting surfaces. Furthermore, the axial force F1 is greater than the retention force of the holding clamps 16.6 on the front case 2.1.

As it is shown in FIGS. 6A and 6B, for example, the back-assembling tool 18 is inserted into the front case 2.1 until it contacts the carrier rear end 16.4. Afterwards, the back-assembling tool 18 is pushed onto the syringe carrier 16 axially forwards so that the syringe carrier 16 is released from the case 2 and moves together with the syringe 3 in a forward direction. As best seen in FIG. 6B, the arms 18.1 of the back-assembling tool 18 are attached to the syringe carrier 16. The carrier rear end 16.4 comprises an elliptical or oval form and has an outer diameter, in part, larger than the outer diameter of the syringe flange 3.1.

Due to the axial force according to the arrow F1 acting on the syringe carrier 16, the holding clamps 16.6 are released from the slots 2.1.1 so that the carrier 16 together with the syringe 3 is moved forwardly. The syringe 3 follows this downward or forward movement.

Figure 7:
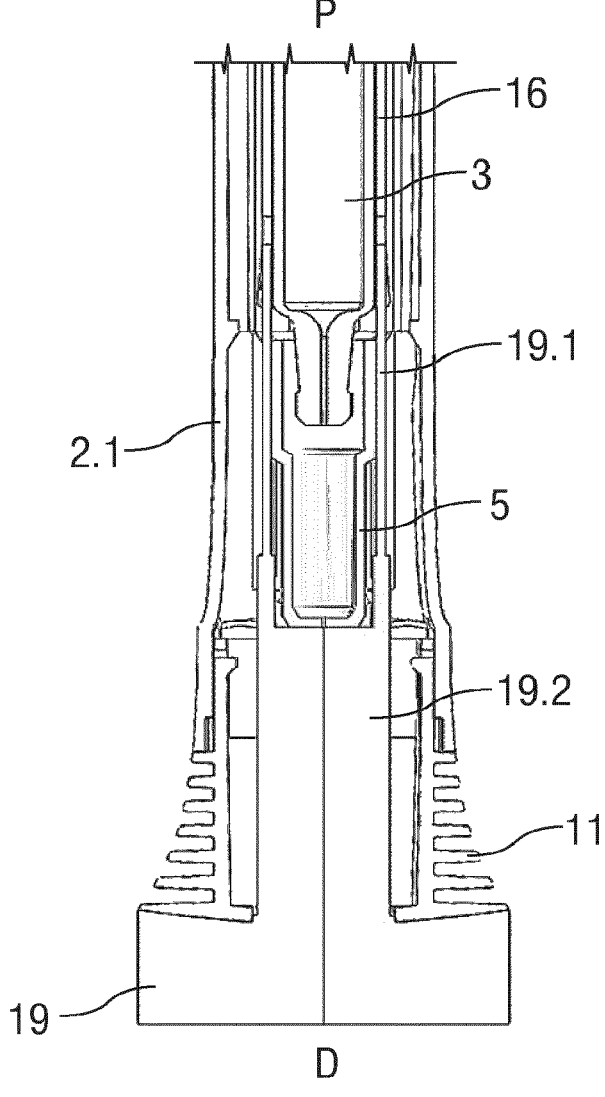
FIGS. 7, 8A, 8B are schematic enlarged partial views of the front subassembly with an arranged front-assembling tool.

When acting an axial force F1 on the syringe carrier 16 the syringe carrier 16 with the syringe 3 is moved forwards within the case 2 until the syringe 3, in particular the protective needle sheath 5, engages and comes in contact with the inserted front-assembling tool 19, so that the syringe 3 is stopped and fixed, as shown in FIGS. 6C and 7.

FIG. 7 shows the engagement of the distal end of the protective needle sheath 5 with a stamp 19.2 of the front-assembling tool 19 so that the syringe 3 is stopped and fixed in the front case 2.1.

Figure 8A:
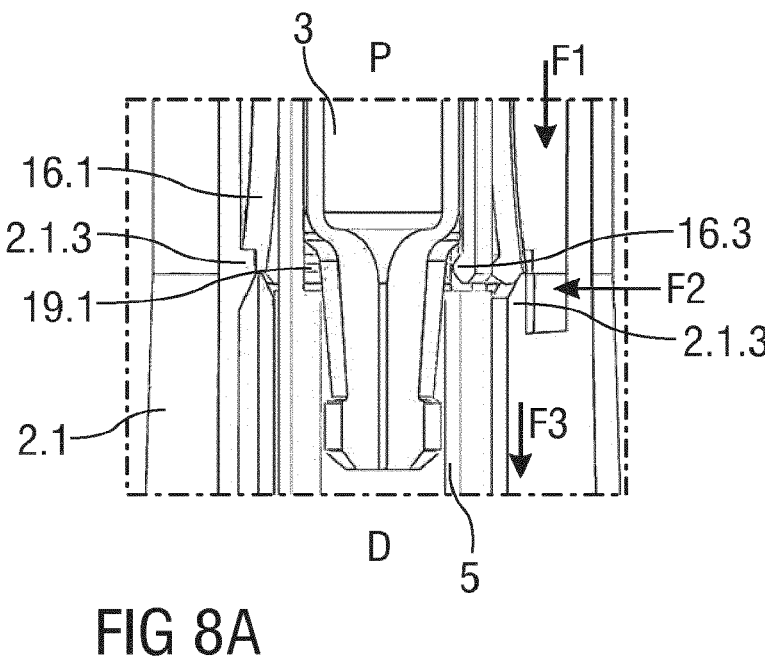
Figure 9:
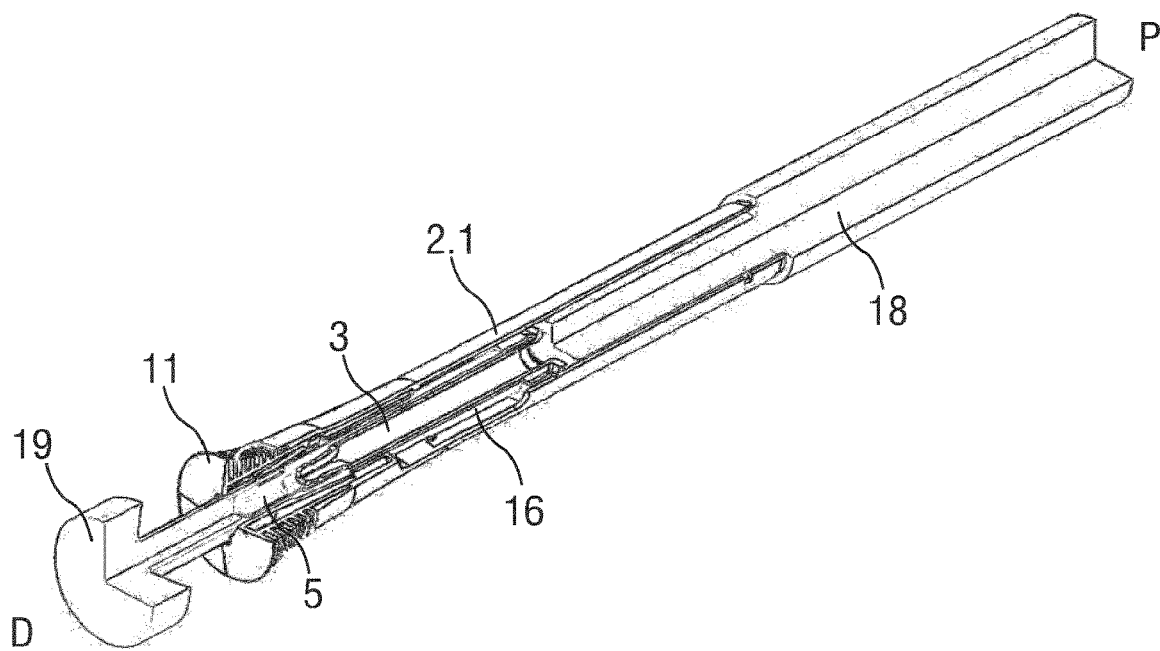
FIG. 9 is a schematic perspective view of an exemplary embodiment of the finally positioned front subassembly.

FIG. 8A shows the further assembling step, wherein the back-assembling tool 18 is further pushed onto the syringe carrier 16 so that the syringe carrier 16 is further moved with respect to the syringe 3 within the case 2, until the syringe carrier 16 also comes in contact with the front-assembling tool 19. In particular, the arms 19.1 are inserted into the distal end of the syringe carrier 16 until the arms 19.1 engage inner edges 16.9 of the syringe carrier 16, as shown in FIG. 7. Due to further axial force F1 to the syringe carrier 16, the front-assembling tool 19 is also moved forwards and extends partially out of the cap 11, as best seen in FIG. 9.

At this point, the flexible arms 16.1 are ready to engage the front case 2.1, in particular the edge 2.1.3. The edge 2.1.3 is formed as a ramp, e.g. a guiding ramp to control the inward deflection of the flexible arms 16.1. The flexible arms 16.1 enter the ramps and are deflected inwards to couple with the distal end of the syringe 3 in the final mounted position. The movement of the syringe carrier 16 is stopped as the ribs 16.8 on the back of the flexible arms 16.1 engage a cut end or nut end arranged in the front case 2.1.

In this final mounted position, the flexible arms 16.1 engage and displace the protective needle sheath 5 to allow space to support the syringe 3 in the final position and at the datum. Furthermore, in this final mounted position, the case 2, in particular the ramp, is adapted to restrain and support the inward deflection of the flexible arms 16.1, forcing the syringe 3 and the protective needle sheath 5 apart.

During assembling and providing the axial force Fl onto the syringe carrier 16, the flexible arms 16.1 are inwardly deflected and restrained in the mounted position by the edge 2.1.3 according to arrow F2 so that the protective needle sheath 5 is displaced according to arrows F3 to allow space between the syringe 3 and the protective needle sheath 5 and to support and position the syringe 3 in the final mounted position. Alternatively, the radially inwards deflected flexible arms 16.1 are positioned a distance from the proximal end of the protective needle sheath 5, e.g. in a distance of minus 0.3 mm.

Figure 8B:
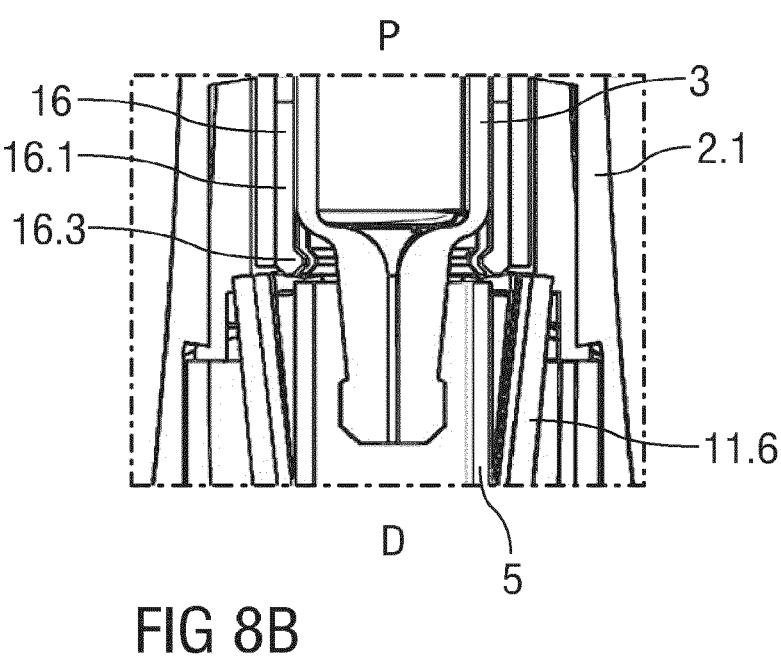

As shown in FIG. 8B, in the final mounted position, the flexible arms 16.1 of the syringe carrier 16 are rigidly held and stable by the edge 2.1.3 of the front case 2.1 to safely support and position the syringe 3.

FIG. 9 shows the syringe carrier 16 and the syringe 3 in the final mounted position. The front-assembling tool 19 is partially pushed out of the cap 11.

Figure 10:
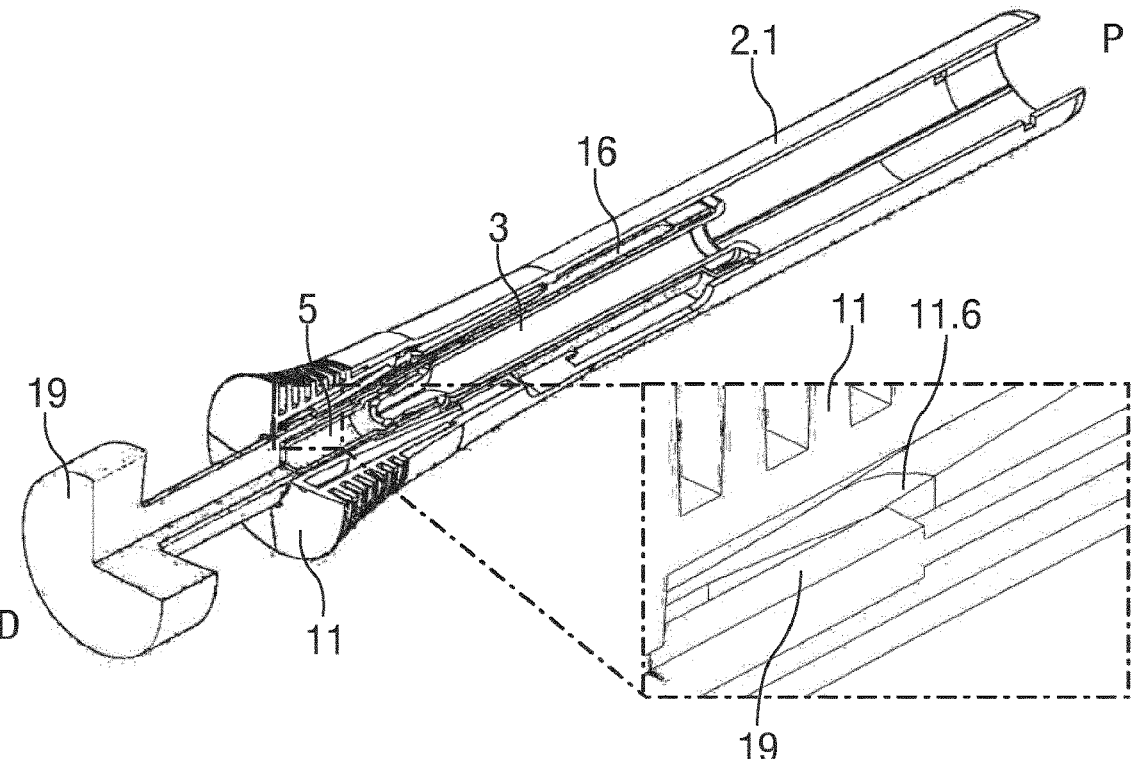
FIG. 10 is a schematic perspective view of an exemplary embodiment of the finally positioned front subassembly with removed back-assembling tool and partially removed front-assembling tool.
Figure 11:
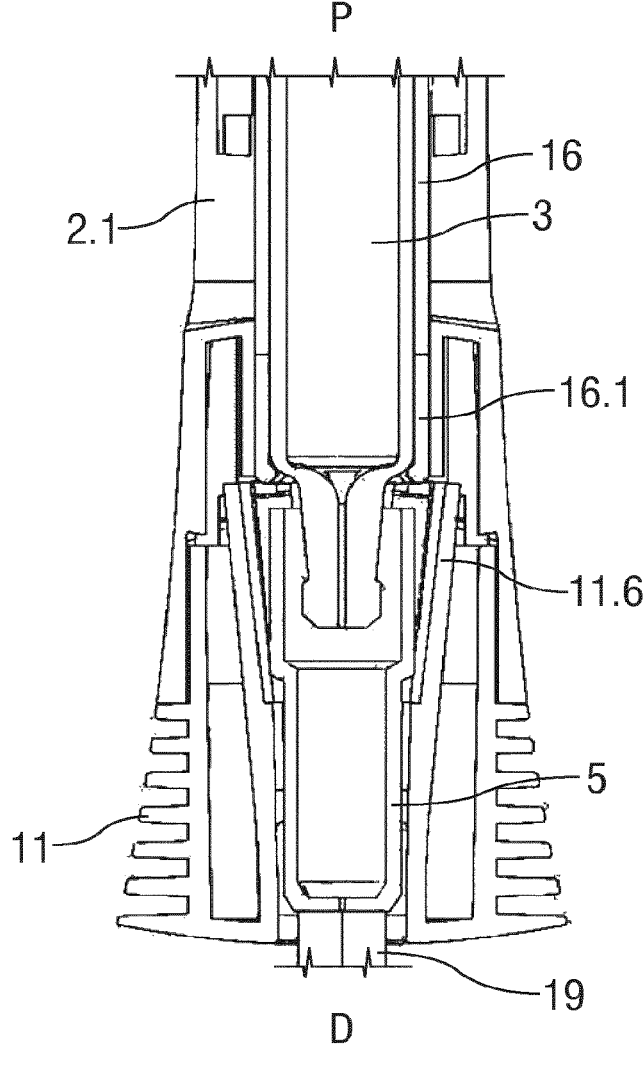
FIG. 11 is a schematic enlarged partial view of the finally assembled front subassembly.

FIG. 10 shows the further assembling step wherein the back-assembling tool 18 is removed. The length of the syringe carrier 16 may be smaller than the length of the syringe 3 to be assembled. The front-assembling tool 19 is further removed from the cap 11 enabling the protective needle sheath 5, as well as the syringe 3 and the syringe carrier 16, due to the engagement of the inwardly deflected arms 16.1 onto the distal end of the syringe 3, to move and fall into the cap 11. Due to the inserted front-assembling tool 19, cap arms 11.6 are deflected outwards as shown in FIG. 11 to support the further movement of the syringe 3 and the syringe carrier 16 into the cap 11.

Due to this further movement of the syringe 3 into the distal direction D, the distal end (datum) of the syringe 3 hits the flexible arms 16.1 of the syringe carrier 16 in the final mounting position.

Figure 12:
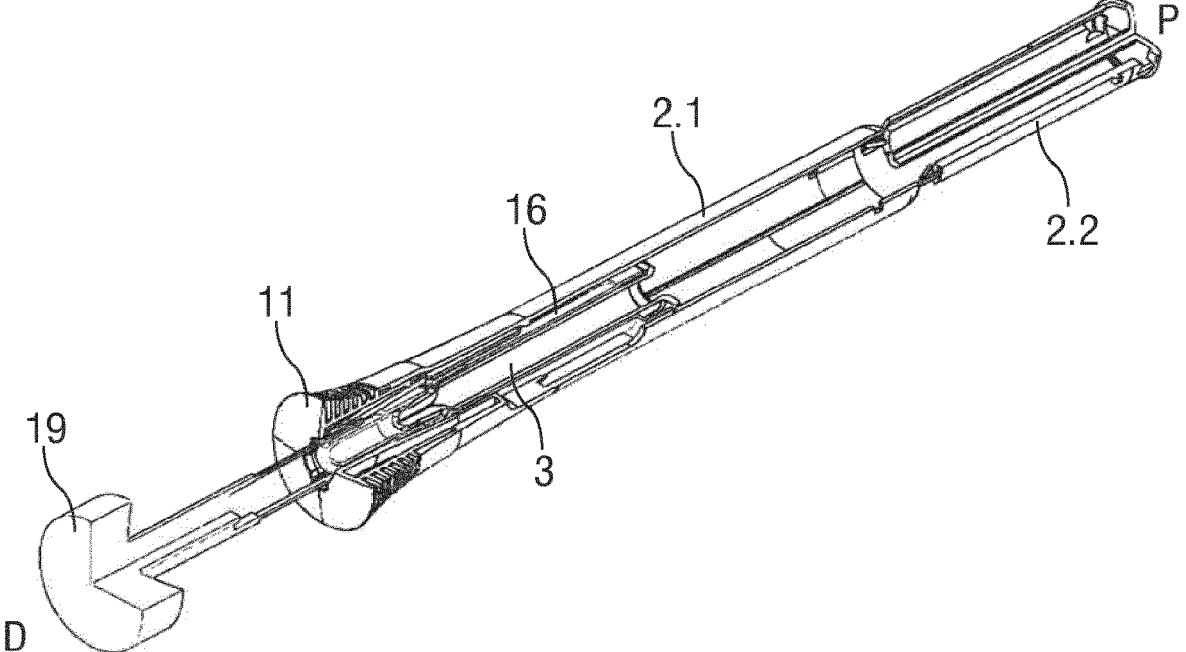
FIG. 12 is a schematic exploded view of a front subassembly and a back subassembly.
Figure 13:
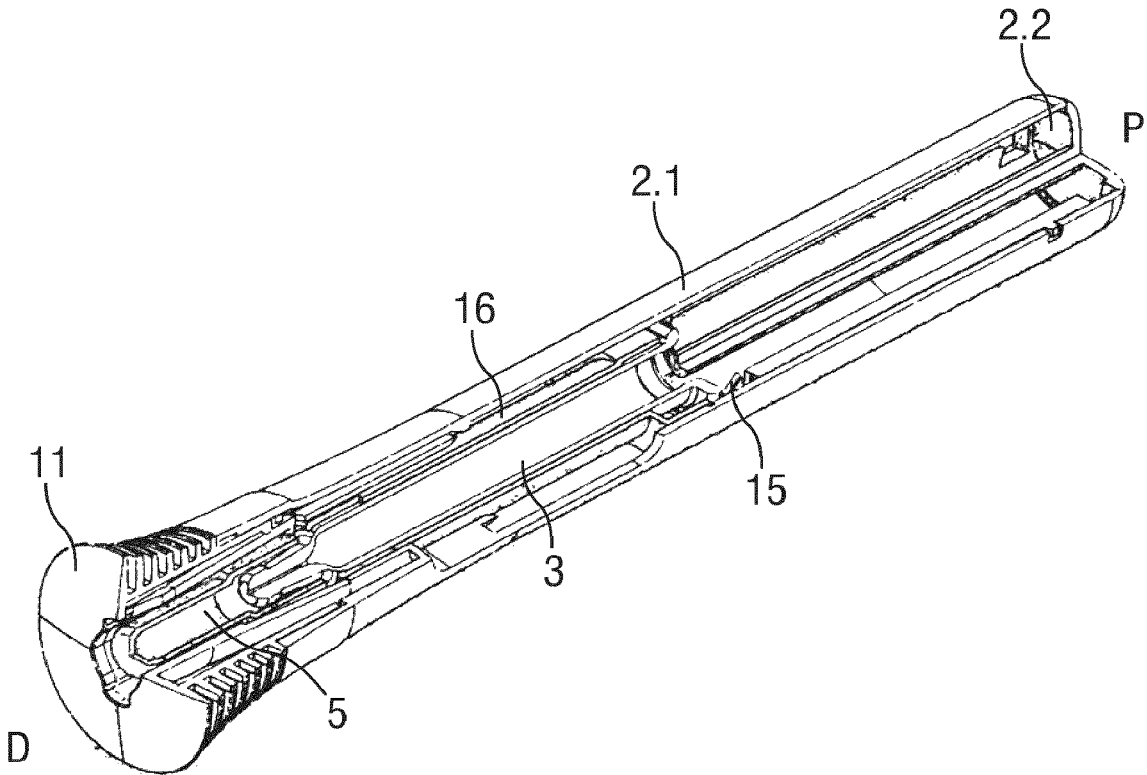
FIG. 13 is a schematic perspective view of the assembled front subassembly and back subassembly.
Figure 14:
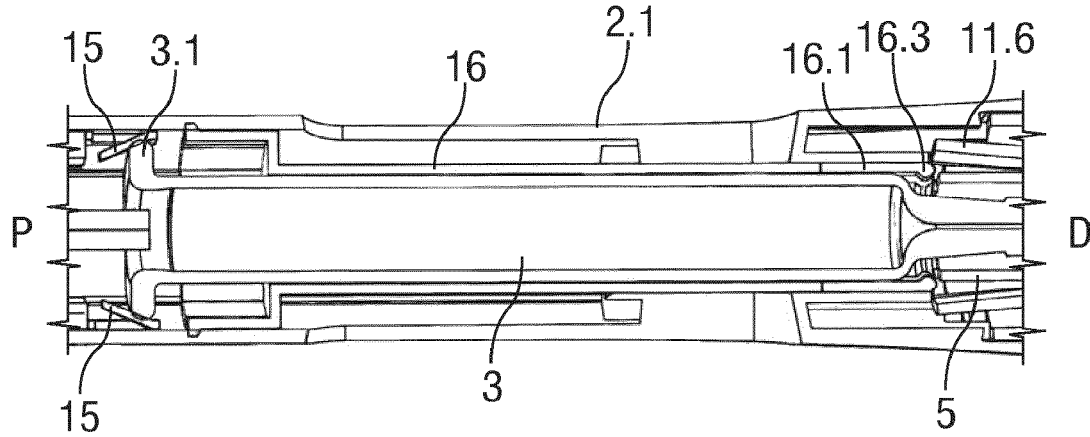
FIG. 14 is schematic enlarged partial view of the distal end of the finally assembled back subassembly.
Figure 15:
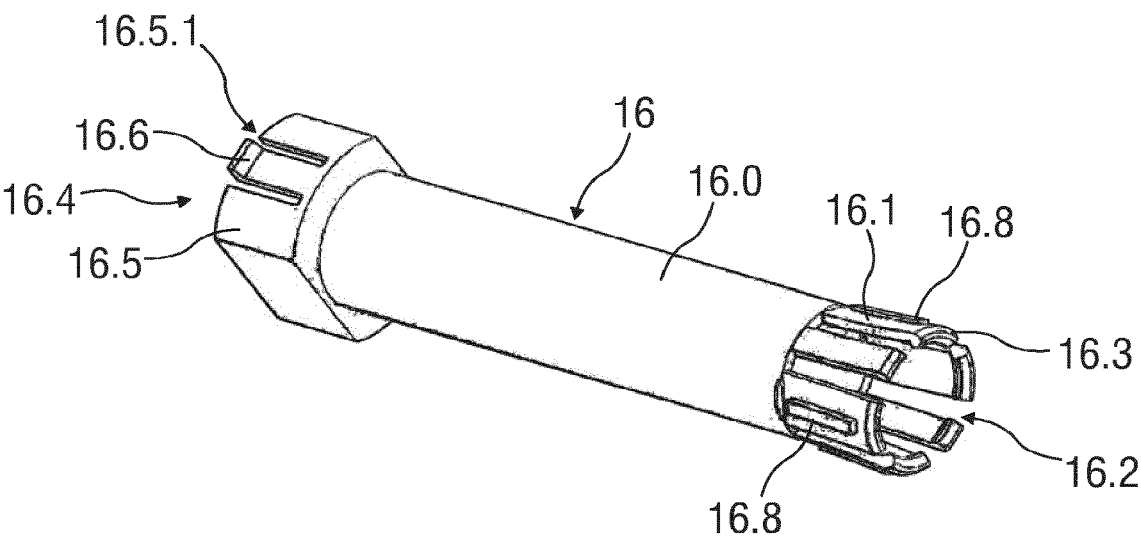
FIG. 15 is a schematic perspective view of an exemplary embodiment of a syringe carrier.

FIGS. 12 to 14 show the last assembling step, wherein the front assembling tool 19 is completely removed, allowing the cap arms 11.6 to close up and engage on the protective needle sheath 5.

The rear case 2.2 is ready to insert into the proximal end of the front case 2.1. The resilient arms 15 ensure that the syringe 3 cannot move backwards into the proximal direction P.

here is a risk that, during the last assembling step, the forces from the removing of the front-assembling tool 19, including gravitational force, do not enable the protective needle sheath 5 to fall into the cap 11. Consequently, the syringe 3 does not come into distal contact with the protrusions 16.3 of the flexible arms 16.1 of the syringe carrier 16. In order to solve this issue, the rear case 2.2 could be inserted and pushed on the syringe 3 until the syringe datum contacts the protrusions 16.3

In summary, FIG. 1 shows a longitudinal section of the autoinjector 1 after final assembly, wherein the rear subassembly 1.2 (also called drive subassembly) is mounted onto the front subassembly 1.1.

In an exemplary embodiment, the rear subassembly 1.2 comprises the plunger 10, the drive spring 9 and the rear case 2.2. Those of skill in the art will understand that if the viscosity or volume, for example, of the medicament M in the syringe 3 is changed, only parts of the rear subassembly 1.2 may need to be changed. To assemble the rear subassembly 1.2, the drive spring 9 is inserted into the plunger 10 and the plunger 10 is inserted in the rear case 2.2 in the proximal direction P, thereby compressing the drive spring 9. Once the plunger 10 and the drive spring 9 reach a compressed position, it is rotated by an angle, e.g. approximately 30° relative to the rear case 2.2, to engage the plunger 10 to the rear case 2.2. In an exemplary embodiment, the rear case 2.2 may have a cam surface to engage the plunger 10 to induce this rotation prior to the plunger 10 and the drive spring 9 reaching the compressed position.

In an exemplary embodiment, after the final assembly of the rear subassembly 1.2 to the front subassembly 1.1, the autoinjector 1 may be kept in temperature controlled environment (e.g., cold chain storage) to, for example, reduce creep in highly stressed components, e.g. under load from the drive spring 9.

In an exemplary embodiment, a force required to press the needle shroud 7 may be approximately 2 N to 12 N. Likewise, the mechanism may work with a higher force.

In an exemplary embodiment, the syringe 3 used in the autoinjector 1 may be a syringe capable of containing approximately 1 mL of the medicament M. In another exemplary embodiment, the syringe 3 used in the autoinjector 1 may be a syringe capable of containing approximately 2 mL of the medicament M.

The autoinjector 1 according to the present disclosure may have an increased shelf-life compared to conventional autoinjectors, because, for example, only the plunger 10 is subjected to the relatively high force of the drive spring 9.

The autoinjector 1 according to the present disclosure may be used as a platform as the drive spring 9 can be changed to alter a force applied to the plunger 10, e.g. for delivering medicaments with different viscosities drugs or reconstituted medicaments, or changing a time required to inject a dose of the medicament.

The cap 11 is suitable for being applied with any kind of injection device or autoinjector. The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro;

Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')₂ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present invention encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

REFERENCE LIST 1 autoinjector
1.1 front subassembly
1.2 rear subassembly
2 case
2.1 front case
2.1.1 slots
2.1.2 distal end of front case
2.1.3 edge
2.2 rear case
2.15 radial stop
3 syringe
3.1 syringe flange
4 needle
5 protective needle sheath
6 stopper
7 needle shroud
8 shroud spring
9 drive spring
10 plunger
11 cap
11.1 grip features
11.2 grip element
11.3 compliant beams
11.4 rib
11.5 opening
11.6 cap arm
12 plunger release mechanism
13 audible indicator
14 shroud lock mechanism
15 resilient arms
16 syringe carrier
16.0 housing
16.1 flexible arms
16.2 carrier front end
16.3 protrusions
16.4 carrier rear end
16.5 carrier flange
16.5.1 proximal shoulder
16.6 holding clamps
16.7 support element
16.8 rib
17 viewing window
18 back-assembling tool
18.1 arms
19 front-assembling tool
19.1 arms
19.2 stamp
F1 to F3 arrow
D distal end
M medicament
P proximal end
The invention claimed is:

1. An autoinjector comprising:
a syringe carrier comprising:
 a housing of the syringe carrier adapted to receive a syringe having a needle encapsulated by a distal removable protective needle sheath, and
 two or more flexible arms extending distally from the housing of the syringe carrier and adapted to couple with the syringe in a mounted position;
a case adapted to receive the syringe carrier;

the syringe; and
the distal removable protective needle sheath,
wherein the two or more flexible arms extend distally from a distal end of the housing of the syringe carrier, and
wherein the syringe carrier is formed as a single part comprising the housing of the syringe carrier and the two or more flexible arms,
wherein the case comprises at least one inwardly directed edge configured to force the syringe and the distal removable protective needle sheath apart by operating onto the two or more flexible arms.

2. The autoinjector according to claim 1, wherein the two or more flexible arms are configured to deflect inwardly, and an inward deflection of the two or more flexible arms is provided in the mounted position by a control feature arranged on the case.

3. The autoinjector according to claim 1, wherein the two or more flexible arms comprise, at their distal ends, inwardly directed protrusions configured to couple with a distal shoulder of the syringe in the mounted position.

4. The autoinjector according to claim 3, wherein an inner diameter of the protrusions is smaller than an outer diameter of the distal removable protective needle sheath and an outer diameter of a shaft of the syringe.

5. The autoinjector according to claim 1,
wherein the housing of the syringe carrier includes a proximal aperture having two opposite straight portions with an outer diameter, in part, smaller than an outer diameter of a proximal syringe flange of the syringe.

6. The autoinjector according to claim 1, wherein the case is adapted to inwardly deflect the two or more flexible arms in the mounted position.

7. The autoinjector according to claim 1, wherein the at least one inwardly directed edge of the case is formed as a ramp.

8. The autoinjector according to claim 1, wherein the case comprises one or more apertures to allow insertion of at least one assembly tool for applying a force to release at least one holding clamp of the syringe carrier from the case and to move the syringe carrier within the case.

9. The autoinjector according to claim 8, wherein at least one aperture of the one or more apertures allows an insertion of at least one front-assembly tool.

10. The autoinjector according to claim 1, wherein the housing of the syringe carrier includes a proximal carrier flange comprising a proximal aperture, and wherein the proximal carrier flange comprises holding clamps with outwardly directed holding features.

11. The autoinjector according to claim 10, wherein the holding clamps are integrally formed on the proximal carrier flange as tongues, and
wherein proximal ends of the holding clamps are outwardly directed forming the holding features.

12. The autoinjector according to claim 10, wherein the holding clamps extend in a first direction that is opposite to a second direction in which the two or more flexible arms extend.

13. The autoinjector according to claim 1, wherein each of the two or more flexible arms extends away from a main part of the housing of the syringe carrier towards a free end of the respective flexible arm.

14. The autoinjector according to claim 1, wherein the two or more flexible arms are arranged stationary relative to the housing of the syringe carrier.

15. The autoinjector according to claim 1, wherein the two or more flexible arms are configured to be arranged stationary relative to the case of the autoinjector during use of the autoinjector.

16. The autoinjector according to claim 1, wherein the syringe comprises a drug.

17. A method of assembling an autoinjector, the method comprising:

inserting and pre-positioning a syringe axially into a syringe carrier mounted in a case, the syringe having a needle encapsulated by a removable protective needle sheath, the syringe carrier comprising two or more flexible arms extending distally from a housing of the syringe carrier and adapted to couple with the syringe in a mounted position;

inserting a front-assembly tool at a distal end of the case and a back-assembly tool at a proximal end of the case; and mounting the syringe into the syringe carrier by releasing the syringe carrier from the case using the back-assembly tool and moving the syringe carrier forward within the case using the back-assembly tool, wherein the case comprises at least one inwardly directed edge configured to operate onto the two or more flexible arms and force the syringe and the removable protective needle sheath apart.

18. The method according to claim 17, wherein inserting the syringe into the syringe carrier comprises moving the syringe axially forward into an opened carrier rear end of the syringe carrier until a syringe flange of the syringe engages the opened carrier rear end.

19. The method according to claim 18, wherein, when inserting the syringe into the syringe carrier, the back-assembly tool is pushed axially forward onto the syringe.

20. The method according to claim 17, wherein mounting the syringe into the syringe carrier comprises pushing the back-assembly tool axially forward onto the syringe carrier so that the syringe carrier moves together with the syringe in a forward direction.

21. The method according to claim 20, wherein, in response to moving the syringe carrier in the forward direction, the syringe carrier reaches the mounted position in the case where the case inwardly deflects the two or more flexible arms of the syringe carrier, forcing the syringe and the removable protective needle sheath apart.

22. A method of delivering a drug from a drug delivery device, wherein the drug delivery device comprises:

a syringe carrier comprising:

a housing of the syringe carrier adapted to receive a syringe having a needle encapsulated by a distal removable protective needle sheath, and two or more flexible arms extending distally from the housing of the syringe carrier and adapted to couple with the syringe in a mounted position;

a case adapted to receive the syringe carrier;

the syringe; and the distal removable protective needle sheath, wherein the two or more flexible arms extend distally from a distal end of the housing of the syringe carrier, wherein the syringe carrier is formed as a single part comprising the housing of the syringe carrier and the two or more flexible arms, and wherein the case comprises at least one inwardly directed edge configured to force the syringe and the distal removable protective needle sheath apart by operating onto the two or more flexible arms, the method comprising:

coupling the two or more flexible arms of the syringe carrier with the syringe in the mounted position of the syringe, wherein the two or more flexible arms extend distally from the housing of the syringe carrier; and moving a plunger of the drug delivery device relative to the housing of the syringe carrier to deliver a dose of the drug from the syringe.

* * * * *